US008206959B2

(12) United States Patent
Shaw

(10) Patent No.: US 8,206,959 B2
(45) Date of Patent: Jun. 26, 2012

(54) PROCESSING ENZYMES FUSED TO BASIC PROTEIN TAGS

(75) Inventor: Allan Christian Shaw, Copenhagen (DK)

(73) Assignee: Novo Nordisk Health Care AG, Zurich (CH)

( * ) Notice: Subject to any disclaimer, the term of this patent is extended or adjusted under 35 U.S.C. 154(b) by 0 days.

(21) Appl. No.: 12/944,400

(22) Filed: Nov. 11, 2010

(65) Prior Publication Data

US 2011/0070610 A1 Mar. 24, 2011

Related U.S. Application Data

(62) Division of application No. 12/443,694, filed as application No. PCT/EP2007/060908 on Oct. 12, 2007, now Pat. No. 7,858,338.

(60) Provisional application No. 60/851,952, filed on Oct. 16, 2006.

(30) Foreign Application Priority Data

Oct. 13, 2006 (EP) .................................. 06122266

(51) Int. Cl.
*C12N 9/00* (2006.01)
(52) U.S. Cl. ........ 435/183; 435/189; 435/193; 435/195; 435/232; 435/233
(58) Field of Classification Search ........................ None
See application file for complete search history.

(56) References Cited

U.S. PATENT DOCUMENTS

| 4,880,911 | A | 11/1989 | Brewer et al. | |
|---|---|---|---|---|
| 5,322,930 | A | 6/1994 | Tarnowski et al. | |
| 5,532,142 | A * | 7/1996 | Johnston et al. | 435/69.1 |
| 2008/0255025 | A1* | 10/2008 | Ladner | 514/2 |
| 2009/0306352 | A1 | 12/2009 | Shaw et al. | |

FOREIGN PATENT DOCUMENTS

| JP | 2006-096713 | 4/2006 |
|---|---|---|
| WO | WO 00/06343 | 2/2000 |
| WO | WO 02/18447 | 3/2002 |
| WO | WO 2006/108826 | 10/2006 |

OTHER PUBLICATIONS

Kuhlman et al. Structure and Stability of the N-terminal domain of the ribosomal protein L9: evidence for rapid two-state folding. Biochemistry 37, 1025-1032.*
Database: Uniport, Accession No. QWZW7 (2006).*
Final Office Action mailed Feb. 25, 2011 for U.S. Appl. No. 11/911,563, filed Oct. 15, 2007 by Shaw et al.
Bi et al, Protein Expression and Purification, 2006, vol. 47, pp. 234-240.
Boime, I et al, Database Genese Q, 2001, EBI accession No. GSP: AAE04488.
Boime, I et al, Database Genese Q, 2001, EBI accession No. GSP: AAE04505.
Copeland, A et al, Database Uniprot, 2006, EBI accession No. AOLWU2.
Copeland, A et al, Database Uniprot, 2007, EBI accession No. A6LMW8.
Erfle, V. et al, Database Genese Q, 2004, EBI accession No. GSP: ADO57970.
Graslund, T. et al., "Integrated Strategy for Selective Expanded Bed Ion-Exchange Adsorption and Site-Specific Protein Processing Using Gene Fusion Technology", Journal of Biotechnology, 2002, vol. 96, No. 1, pp. 93-102.
Graslund, T. et al., "Charge Engineering of a Protein Domain to Allow Efficient Ion-Exchange Recovery", Protein Engineering, 2000, vol. 13, No. 10, pp. 703-709.
Graslund, T. et al., "Strategy for Highly Selective Ion-Exchange Capture Using a Charge-Polarizing Fusion Partner", Journal of Chromatography, 2002, vol. 942, No. 1-2, pp. 157-166.
Henne, A et al, Database Uniprot, 2004, EBI accession No. Q72GV5.
Kuboki, Y et al, Database Genese Q, 2006, EBI accession No. AEH09114.
Kuhlman et al., "Structure and Stability of the N-Terminal Domain of the Ribosomal Protein L9: Evidence for Rapid Two-State Folding", Biochemistry, 1998, No. 37, pp. 1025-1032.
Kuhlman, B. et al, Journal of Molecular Biology, 1998, vol. 284, Part 5, pp. 1661-1670.
Machine Translation of JP 2006-096713, published Apr. 13, 2006.
Nelson et al., UniProt Accession No. Q9WZW7, publically available Nov. 1, 1999.
Neumann, M. et al, Database EPO Proteins, 2003, EPOP accession No. AX589447.
Non-Final Office Action mailed Jul. 13, 2010 for U.S. Appl. No. 11/911,563, filed Oct. 15, 2007 by Shaw et al.
Shin et al., Journal of Biotechnology, 1998, vol. 62, pp. 143-151.
Takami, H. et al, Database Uniprot, 2005, EBI accession No. Q5KU74.
Terpe, K, Applied Microbiology and Biotechnology, 2003, vol. 60, Part 5, pp. 523-533.
Copeland, A et al, Ribosomal Protein L9, Database Uniprot, 2007, EBI accession No. ABR31269.1, Jun. 26, 2007.
Henne, A et al, 50S Ribosomal Protein L9, Database Uniprot, 2004, EBI accession No. Q72GV5.1, Jul. 5, 2004.
Nelson, K.E. et al, 50S Ribosomal Protein L9, Database Uniprot, 2000, EBI accession No. Q9WZW7.1, Feb. 15, 2000.
Takami, H. et al, 50S Ribosomal Protein L9, Database Uniprot, 2004, EBI accession No. YP149330.1, Dec. 8, 2004.
Yuan Bi, et al., "Efficient High Level Expression of Peptide and Proteins as Fusion Proteins With the N-Terminal Domain of L9 Application to the Villin Headpiece Helical Subdomain," Protein Expression and Purification, 2005, vol. 47, pp. 234-240.
Elke, et al, Biological Chemistry Hoppe Seyler, The Amino Acid Sequences of the *Bacillus stearo thermophilus* Ribosomal Protein SS17 and S21 and Their Comparison to Homologus Proteins od Other Ribosomes, 1991, vol. 372, pp. 955-961.
Kazutomo, et al, Dictionary of Biochemistry, 2002, vol. 3, p. 1489.
Klenk HP, et al, Database DDBJ/EMBL/Genbank [online], Definition: LSU Ribosomal Protein L39E(RP139E) [*Archaeoglobus fulgidus* DSM4304], 2004, EBI accession No. NP_070891.

* cited by examiner

*Primary Examiner* — Nashaat Nashed
(74) *Attorney, Agent, or Firm* — Teresa Chen

(57) ABSTRACT

The invention is related to processing enzyme comprising an N-terminally attached tag derived from highly basic proteins from thermophilic bacteria. The processing enzymes are useful for modifying proteins. They can be produced in high yields and can be effectively separated from the modified protein after use.

19 Claims, 2 Drawing Sheets

PROCESSING ENZYMES FUSED TO BASIC PROTEIN TAGS

CROSS REFERENCE TO RELATED APPLICATIONS

This application is a divisional application of U.S. patent application Ser. No. 12/443,694, filed May 1, 2009 now U.S. Pat. No. 7,858,338, which is 35 U.S.C. §371 national stage application of International Patent Application PCT/EP2007/060908 (published as WO 2008/043847 A1), filed Oct. 12, 2007, which claimed priority of European Patent Application 06122266.7, filed Oct. 13, 2006; this application further claims priority under 35 U.S.C. §119 of U.S. Provisional Application 60/851,952, filed Oct. 16, 2006.

FIELD OF THE INVENTION

The present invention relates to novel processing enzymes comprising an alkaline protein tag derived from thermophillic bacteria.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Nov. 10, 2010. The Sequence Listing is made up of 48 kilobytes, and the information contained in the attached "SEQUENCE LISTING" is identical to the information in the specification as originally filed. No new matter is added.

BACKGROUND OF THE INVENTION

Expression of recombinant proteins in microbial host cells is widely used for industrial production of human therapeutic proteins. A fusion partner may be attached to the N-terminal (or C-terminal) of the target protein and serves to increase expression level, solubility or correct folding of the target protein and to facilitate easy purification during downstream processing. Removal of the fusion partner from the target protein is mostly necessary in order to conserve the biological activity of the target protein. The processing of the fusion protein can either be performed after expression or after one or more initial purification steps using suitable proteases capable of cleaving the fusion partner to release the target protein. The recombinant target protein with or without a fusion partner may also need to be modified after translation to obtain certain biological features using one or more enzymatic steps. Such modification includes removal of unwanted glycosylations with mannose, fucose or xylose sugars or introductions of glycosylations. Modifications may also include deamidations, amidations, methylations, phosphorylations, dephosphorylations, sulfations, acetylations or transaminations.

To decrease the cost of the down stream processing steps it is pivotal that these processing enzymes are cheap to produce e.g. can be expressed in high amounts and purified with a small number of chromatographic steps. Furthermore it is desirable that processing enzymes used for cleavage of fusion proteins can be easily removed after processing of the target protein. It may also be an advantage that the processing enzymes can be immobilised to purifications columns.

The present invention provides novel processing enzymes which are well suited for modification of target proteins including cleavage of fusion partners from a fusion protein. Furthermore, the novel processing enzymes can easily be separated from the target protein after the processing step.

SUMMARY OF THE INVENTION

In one aspect the invention is related to processing enzymes comprising an N-terminally attached tag derived from highly basic ribosomal proteins from thermophilic bacteria.

Some of these tags are disclosed in copending patent application PCT/EP2006/061493.

The tag will facilitate expression of soluble tagged processing enzyme in high yields. The tag will also enable high purity after a single cation exchange chromatography purification step as well as easy removal of the tagged processing enzyme following processing of the target protein precursor. The tags also enable on-column processing using cation exchange chromatography matrix as immobilizer for the tagged processing enzyme.

With the expression "a highly basic protein" is meant a protein having a high percent of the basic amino acid residues Lys and Arg, e.g. at least about 15% of the total number of amino acid residues in the protein.

With "ribosomal proteins" is meant peptide or polypeptide subunits of the ribosome which are the particles that catalyze mRNA-directed protein synthesis in all organisms. Ribosomal proteins are defined on the basis of their sequence by ribosomal signatures as reported in domain databases such as InterPro and Prosite. The advantage of using ribosomal proteins is that they are mostly very positively charged.

In the present context "thermophilic microorganisms" means organisms which grow optimally at about 50° C. to about 100° C. This is in contrast to mesophiles which in general grow optimally at temperatures from 30-37° C. The term "thermophilic bacteria" will in this context cover hyperthermophilic bacteria as well.

In one embodiment the tag contains no cysteine residues.

In a further embodiment the tag comprises from about 15 to about 250, from about 15 to about 225, from 15 to about 200, from about 15 to about 175, from about 15 to about 150, from 15 to about 75, or from about 15 to about 50 amino acid residues.

In one embodiment the tag has from about 15 to about 250 amino acid residues.

In one embodiment the tag has from about 15 to about 200 amino acid residues.

In one embodiment the tag has from about 15 to about 150 amino acid residues.

In one embodiment the tag has from about 15 to about 100 amino acid residues.

In one embodiment the tag has from about 15 to about 50 amino acid residues.

In a further embodiment the tag comprises from about 20 to about 120, from about 20 to about 100, from about 20 to about 90, from about 20 to about 75 amino acid residues or from about 20 to about 50 amino acid residues.

In one embodiment the tag has from about 20 to about 120 amino acid residues.

In one embodiment the tag has from about 20 to about 100 amino acid residues.

In one embodiment the tag has from about 20 to about 90 amino acid residues.

In one embodiment the tag has from about 20 to about 75 amino acid residues.

In one embodiment the tag has from about 20 to about 50 amino acid residues.

In one embodiment the tag has from about 50 to about 250 amino acid residues.

In one embodiment the tag has from about 50 to about 225 amino acid residues.

In one embodiment the tag has from about 50 to about 200 amino acid residues.

In one embodiment the tag has from about 50 to about 175 amino acid residues.

In one embodiment the tag has from about 50 to about 150 amino acid residues.

In one embodiment the tag has from about 50 to about 125 amino acid residues.

In one embodiment the tag has from about 50 to about 100 amino acid residues.

In one embodiment the tag has from about 50 to about 75 amino acid residues.

In one embodiment the tag has from about 75 to about 250 amino acid residues.

In one embodiment the tag has from about 75 to about 225 amino acid residues.

In one embodiment the tag has from about 75 to about 200 amino acid residues.

In one embodiment the tag has from about 75 to about 175 amino acid residues.

In one embodiment the tag has from about 75 to about 150 amino acid residues.

In one embodiment the tag has from about 75 to about 125 amino acid residues.

In one embodiment the tag has from about 75 to about 100 amino acid residues.

In one embodiment the tag has from about 100 to about 250 amino acid residues.

In one embodiment the tag has from about 100 to about 225 amino acid residues.

In one embodiment the tag has from about 100 to about 200 amino acid residues.

In one embodiment the tag has from about 100 to about 175 amino acid residues.

In one embodiment the tag has from about 100 to about 150 amino acid residues.

In one embodiment the tag has from about 100 to about 125 amino acid residues.

The tag will typically contain from at least about 15% basic amino acid residues and the purification tag may contain from about 15 to about 50%, from about 15 to about 45%, from about 15 to about 40, from about 15 to about 35%, from about 15 to about 30%, from about 15 to about 25% or from about 15 to about 20% basic amino acid residues.

In another embodiment the tag comprises from about 20 to about 50%, from about 20 to about 40% or from about 20 to about 30 basic amino acid residues.

In another embodiment the tag comprises from about 40% to about 50% basic amino acid residues.

In another embodiment the tag comprises from about 40% to about 60% basic amino acid residues, Lys and Arg.

In one embodiment the tag comprises from 15 to 50% basic amino acid residues.

In another embodiment the tag comprises from 15 to 45% basic amino acid residues.

In another embodiment the tag comprises from 15 to 40% basic amino acid residues.

In another embodiment the tag comprises from 15 to 35% basic amino acid residues.

In another embodiment the tag comprises from 15 to 30% basic amino acid residues.

In another embodiment the tag comprises from 15 to 25% basic amino acid residues.

In another embodiment the tag comprises from 15 to 20% basic amino acid residues.

In one embodiment the tags are derived from the a ribosomal protein L9 family, which is one of the proteins of the large ribosomal subunit, as described in, for example, the Prosite data base (Hulo N., Bairoch A., Bulliard V., Cerutti L., De Castro E., Langendijk-Genevaux P. S., Pagni M., Sigrist C. J. A. "The PROSITE database." Nucleic Acids Res. 34:D227-D230 (2006).

In one embodiment of the invention the tag is selected from the group of peptide sequences consisting of (SEQ ID NO: 1)
MSKTIVRKNESIDDALRRFKRAVSKTGTLQEVRKREFYEKPSVRRKKKSE

AARKRK;

(SEQ ID NO: 2)
MGKKTVGVKKRLAKAYKQNRRAPVWITVKTKRSVFGSPKRRHWRRSKLK

V;

(SEQ ID NO: 3)
MKRTYQPSRRKRKRTHGFLARKRTPGGRRVLKNRRRKGRWRLTV;

(SEQ ID NO: 4)
MGKGDRRTRRGKIWRGTYGKYRPRKKK;

(SEQ ID NO: 5)
MAKVKMKTNRSAAKRFKVTAKGKIKRWKSGGAHYNTKKSSKRKRHLRKHT

YVKDNMLKHVKALLKEF;

(SEQ ID NO: 6)
MPKHSKRYLEARKLVDRTKYYDLDEAIELVKKTATAKFDETIELHIQTGI

DYRKPEQHIRGTIVLPHGTGKEVKVLVFAKGEKAKEALEAGADYVGAEDL

VEKIEKEGFLDFDVAIATPDMMRIIGRLGKILGPRGLMPSPKSGTVTQEV

AEAVKEFKKGRIEVRTDKTGNIHIPVGKRSFDNEKLKENIIAAIKQIMQM

KPAGVKGQFIKKVVLASTMGPGIKLNLQSLLKE, (SEQ ID NO: 7)
MAQVDLLNVKGEKVGTLEISDFVFNIDPNYDVMWRYVDMQLSNRRAGTAS

TKTRGEVSGGGRKPWPQKHTGRARHGSIRSPIWRHGGVVHGPKPRDWSKK

LNKKMKKLALRSALSVKYRENKLLVLDDLKLERPKTKSLKEILQNLQLSD

KKTLIVLPWKEEGYMNVKLSGRNLPDVKVIIADNPNNSKNGEKAVRIDGL

NVFDMLKYDYLVLTRDMVSKIEEVLGNEAGKALTA, (SEQ ID NO: 8)
MRYEYVPLKDQYEKEIVPALMKEFNYKNIHQVPKLVKIVINMGIGEG

SRNYDLIERHANELAKITGQKPIVTRARKSISNFKIRKGMPIGLKVT

LRGARMYNFLYKLINIVLPKVRDFRGLDPNSFDGRGNYSFGLSEQLV

FPELNPDEVRRIQGMDITIVTTAKTDQEARRLLELFGMPFKRG, (SEQ ID NO: 9)
MSRLAKKPIVLPQGVTVEIKDNVVKVKGPKGELSQEFLPYVKIEVEGNEV

WVRPNEEQIIRKSDWRKVKMFQGTYWSLIRNMVVGVTEGYKKELEIVGIG

YRAQLQGNTLVMNLGYAHPVVYEIPSDVKIEVPAPNRIIVSGIDKQRVGQ

VAAEIRAFRPPNVYTGKGIRYVGEVVRQKEGKKA, (SEQ ID NO: 10)
MKVILLRDVPKIGKKGEIKEVSDGYARNYLIPRGFAKEYTEGLERAIKHE

KEIEKRKKEREREESEKILKELKKRTHVVKVKAGEGGKIFGAVTAATVAE

```
                                     (SEQ ID NO: 11)
EISKTTGLKLDKRWFKLDKPIKELGEYSLEVSLPGGVKDTIKIRVEREE, (SEQ ID NO: 12)
MLTRQQKELIVKEMSEIFKKTSLILFADFLGFTVADLTELRSRLREKYGD

GARFRVVKNTLLNLALKNAEYEGYEEFLKGPTAVLYVTEGDPVEAVKIIY

NFYKDKKADLSRLKGGFLEGKKFTAEEVENIAKLPSKEELYAMLVGRVKA

PITGLVFALSGILRNLVYVLNAIKEKKSE, (SEQ ID NO: 13)
MARYFPVQKTTMIKPEEVERKWYVVDASGKVLGRLATRIAKILMGKHKPN

YTPHVDTGDYVIVVNADKVVLTGKKLDQKVYYWHSGYPGGLKSLTARQML

EKHPERLIWLAVKRMLPKNRKGRKMLKRLKVYASPEHPHQAQKPEPIEL, (SEQ ID NO: 14)
MRLEDLRPTPGAMKKRKRVGRGPGSGHGKTSGRGHKGQKARGSGKVHIWF

EGGQTPLQRRLPKRGFKNINKKVYAVVNVKVLEERFEANEEVTPEKLIER

KIIKDLKDGVKILGDGELTKPLVVKAHAFSKSAVEKIESAGGKAEVI, (SEQ ID NO: 15)
MRHRVKRHKLGRYGSHRKSLLRNLSREIVEHGSIVTTTAKAKALKTFMDK

LVSKAIEAATTDDRARSVHLRRQINAVLGDRRLTNKLVDEIAKNYVGRRG

GYVRVLRIGFRRGDAAEMSLVQLVEASSQEG, (SEQ ID NO: 15)
MDHLVKIIEKKYEKKEIPDFRPGDTVRVHVKVIEGDRERTQVFEGIV

IAKRGSGINKTFTVRRIGSHGVGVERIFPVHSPVVEKIEVVRKGKVR

RAKLYYLRNVRGKIRKIKERRD, (SEQ ID NO: 16)
MRVKRAVHAKKKRKKYLKAAKGYRGALSRRYKLAKQMYVRSKWYSYVGRK

QKKRDMRKLWITRINIAARNEGLKYSELIHGLKLAGVSINRKMLSELAVN

DPEAFKEYVKIAKEALAS, (SEQ ID NO: 17)
MLYAIVETAGRQYRVEEGKILYTEKQKDYSPGDEIVFDRVVFVRKDGEVL

VGKPYVEGAKVVGKVLEHAKARKVKTVKYRPRKNSKVEKGHRQWYTAIKI

EKIEL, (SEQ ID NO: 18)
MKQEKLSLHDVLIRPIITEKALILREQRKYVFEVNPLANKNLVKEAV

EKLFNVKVEKVNILNMKPKPKRRGIFEGKTRSWKKAVVTLKEGYTIK

ELEGEH, (SEQ ID NO: 19)
MAHKKSGGVAKNGRDSLPKYLGVKVGDGQIVKAGNILVRQRGTRFYPGKN

VGMGRDFTLFALKDGRVKFETKNNKKYVSVYEE, (SEQ ID NO: 20)
MKASELRNYTDEELKNLLEEKKRQLMELRFQLAMGQLKNTSLIKLTKRDI

ARIKTILRERELGIRR, (SEQ ID NO: 21)
MPKKLKIKLVKSPIGYSWDQKDTVKRLGLKKLNQVVIKDDLPQIRGMIRK

VKHLVEVEEIEEGGSNA, (SEQ ID NO: 22)
MPKVKTNRSAAKRFRITKNGKIMRNHAYRSHKTGKKRRNALRALRKKDVV

SSADKNRVLRLLGKK, (SEQ ID NO: 23)
MGQKVHPRGFRLGLSADWQAKWFNEKNYKEWLLEDEEIRKIIKNKYY

HAGISEIYVERPDAERINITVKTARPGIIIGRKGSEITSLREELERK

FNRRVVINIEEIKTPELDAQLVAESIASRIEKRASYKVAMKRAIMNA

MRKGAQGIKVMVAGRLGGAEIARREWYLRGRLPLQKIKAIIDYGTAT

AWTKYGTIGIKVWIYKGDADI, (SEQ ID NO: 24)
METQGVMKEIQYEEFEEKIIEIRRTSKVTKGGKNLSFRVVAIVGNKNGKV

GLGIGKAREVPEAIRKAISAAKRNIVEVPVINGTIPHEVIGRQDASKVLL

KPAAPGTGIIAGGTVRAVVELAGIQNILTKSLGSTNPLNLALATMNGLKN

LLDPRKVAKLRDISVEEVFKGVRRENNA, (SEQ ID NO: 25)
MVSLDPEKKNEIIKEFQIHENDTGSVEVQIALLTARIKHLTEHLRKHPKD

FHSRRGLMKMIGRRRKMLKYLRHKKPEVYRELIAKLGIRK, (SEQ ID NO: 26)
MGRSRKKGPYVDRKLLEKIRKLNETGEKKVIKTWSRASMIIPEMVGHTIA

VYNGMKHIPVYITENMIGHRLGEFAPTRRFGGHADKKAKKGELKK
and (SEQ ID NO: 27)
MPNIKSAKKRVRVSEKRRLRNKAYKTFFKNRIKEVLKAIENKEPKEVVLE

LTRKAQAAIDKAVSKGVIHKNQGARRKARLFEKVNEYLRTLETTQE.
```

In another embodiment the tag is selected from the group consisting of

```
                                     (SEQ ID NO: 18)
MKQEKLSLHDVLIRPIITEKALILREQRKYVFEVNPLANKNLVKEAVEKL

FNVKVEKVNILNMKPKPKRRGIFEGKTRSWKKAVVTLKEGYTIKELEGEH
and (SEQ ID NO: 19)
MAHKKSGGVAKNGRDSLPKYLGVKVGDGQIVKAGNILVRQRGTRFYPGKN

VGMGRDFTLFALKDGRVKFETKNNKKYVSVYEE.
```

In another embodiment the tag is selected from the group consisting of

```
                                     (SEQ ID NO: 10)
MKVILLRDVPKIGKKGEIKEVSDGYARNYLIPRGFAKEYTEGLERAIKHE

KEIEKRKKEREREESEKILKELKKRTHVVKVKAGEGGKIFGAVTAATVAE

EISKTTGLKLDKRWFKLDKPIKELGEYSLEVSLPGGVKDTIKIRVEREE;

(SEQ ID NO: 15)
MDHLVKIIEKKYEKKEIPDFRPGD-TVRVHVKVIEGDRERTQVFEGIVIA

KRGSGINKTFTVRRIGSHGVGVERIFPVHSPVVEKIEVVRKGKVRRAKLY

YLRNVRGKIRIKERRD
and (SEQ ID NO: 1)
MSKTIVRKNESIDDALRRFKRAVSKTGTLQEVRKREFYEKPSVRRKKKSE

AARKRK.
```

In another embodiment the tag is selected from the group consisting of (SEQ ID NO: 6)
MPKHSKRYLEARKLVDRTKYYDLDEAIELVKKTATAKFDETIELHIQTGI
DYRKPEQHIRGTIVLPHGTGKEVKVLVFAKGEKAKEALEAGADYVGAEDL
VEKIEKEGFLDFDVAIATPDMMRIIGRLGKILGPRGLMPSPKSGTVTQEV
AEAVKEFKKGRIEVRTDKTGNIHIPVGKRSFDNEKLKENIIAAIKQIMQM
KPAGVKGQFIKKVVLASTMGPGIKLNLQSLLKE;

(SEQ ID NO: 7)
MAQVDLLNVKGEKVGTLEISDFVFNIDPNYDVMWRYVDMQLSNRRAGTAS
TKTRGEVSGGGRKPWPQKHTGRARHGSIRSPIWRHGGVVHGPKPRDWSKK
LNKKMKKLALRSALSVKYRENKLLVLDDLKLERPKTKSLKEILQNLQLSD
KKTLIVLPWKEEGYMNVKLSGRNLPDVKVIIADNPNNSKNGEKAVRIDGL
NVFDMLKYDYLVLTRDMVSKIEEVLGNEAGKALTA, (SEQ ID NO: 9)
MSRLAKKPIVLPQGVTVEIKDNVVKVKGPKGELSQEFLPYVKIEVEGNEV
WVRPNEEQIIRKSDWRKVKMFQGTYWSLIRNMVVGVTEGYKKELEIVGIG
YRAQLQGNTLVMNLGYAHPVVYEIPSDVKIEVPAPNRIIVSGIDKQRVGQ
VAAEIRAFRPPNVYTGKGIRYVGEVVRQKEGKKA, (SEQ ID NO: 23)
MGQKVHPRGFRLGLSADWQAKWFNEKNYKEWLLEDEEIRKIIKNKYYHAG
ISEIYVERPDAERINITVKTARPGIIIGRKGSEITSLREELERKFNRRVV
INIEEIKTPELDAQLVAESIASRIEKRASYKVAMKRAIMNAMRKGAQGIK
VMVAGRLGGAEIARREWYLRGRLPLQKIKAIIDYGTATAWTKYGTIGIKV
WIYKGDADI
and (SEQ ID NO: 24)
METQGVMKEIQYEEFEEKIIEIRRTSKVTKGGKNLSFRVVAIVGNKNGKV
GLGIGKAREVPEAIRKAISAAKRNIVEVPVINGTIPHEVIGRQDASKVLL
KPAAPGTGIIAGGTVRAVVELAGIQNILTKSLGSTNPLNLALATMNGLKN
LLDPRKVAKLRDISVEEVFKGVRRENNA, In another embodiment the tag is selected from the group consisting of (SEQ ID NO: 10)
MKVILLRDVPKIGKKGEIKEVSDGYARNYLIPRGFAKEYTEGLERAIKHE
KEIEKRKKEREREESEKILKELKKRTHVVKVKAGEGGKIFGAVTAATVAE
EISKTTGLKLDKRWFKLDKPIKELGEYSLEVSLPGGVKDTIKIRVEREE;

(SEQ ID NO: 41)
MKVILLEPLENLGDVGQVVDVKPGYARNYLLPRGLAVLATESNLKALEAR
IRAQAKRLAERKAEAERLKEILENLTLTIPVRAGETKIYGSVTAKDIAEA
LSRQHGITIDPKRLALEKPIKELGEYVLTYKPHPEVPIQLKVSVVAQE;

(SEQ ID NO: 42)
MKVIFLKDVKGKGKKGEIKDVADGYANNFLFKQGLAIEATPANIKALEAQ
KQKEQRQAAEELANAKKLKEELEKLTVEIPAKAGEGGRLFGSITSKQIAE
ALQAQHGLKLDKRKIELADAIRSLGYTNVPVKLHPEVTATLKVHVKEQK;

(SEQ ID NO: 43)
MKVVLLKDVS KIGKKGEIKN VSDGYARNYLIPKGLALEATPRVLKRLE

AEKR-KKEEEKIQ IKTQNEELLKMLKKFLYKIP VKAGESGKLFGALTN
SDIAK AVEKIADVNIDKKFIVLEKPIKEIGMYDVLVRLPEGVSGK IKV
EVIQEGKN
and (SEQ ID NO: 44)
MKLILTQEVAGLGGPGDVVEVRDGYGRNYLLPKRLAMPASPGAVKQVALI
KRAREVREIRDLDQARALRDQLEALPVTLPARAGSGGRLFGSVTPDDIAA
AVHAAGGPKLDKRRIEISGPIKTIGSHQVTVRLHPEVSATVSVEVVPAS.

In a further embodiment the tag has the sequence (SEQ ID NO: 18)
MKQEKLSLHDVLIRPIITEKALILREQRKYVFEVNPLANKNLVKEA
VEKLFNVKVEKVNILNMKPKPKRRGIFEGKTRSWKKAVVTLKEGYT
IKELEGEH.

In a further embodiment the tag has the sequence (SEQ ID NO: 19)
MAHKKSGGVAKNGRDSLPKYLGVKVGDGQIVKAGNILVRQRGTRFY
PGKNVGMGRDFTLFALKDGRVKFETKNNKKYVSVYEE.

In a further embodiment the tag has the sequence (SEQ ID NO: 15)
MDHLVKIIEKKYEKKEIPDFRPGDTVRVHVKVIEGDRERTQVFEGI
VIAKRGSGINKTFTVRRIGSHGVGVERIFPVHSPVVEKIEVVRKGK
VRRAKLYYLRNVRGKIRIKERRD.

In a further embodiment the tag has the sequence (SEQ ID NO: 10)
MKVILLRDVPKIGKKGEIKEVSDGYARNYLIPRGFAKEYTEGLERAIKHE
KEIEKRKKEREREESEKILKELKKRTHVVKVKAGEGGKIFGAVTAATVAE
EISKTTGLKLDKRWFKLDKPIKELGEYSLEVSLPGGVKDTIKIRVEREE.

In a further embodiment the tag has the sequence (SEQ ID NO: 41)
MKVILLEPLENLGDVGQVVDVKPGYARNYLLPRGLAVLATESNLKALEAR
IRAQAKRLAERKAEAERLKEILENLTLTIPVRAGETKIYGSVTAKDIAEA
LSRQHGITIDPKRLALEKPIKELGEYVLTYKPHPEVPIQLKVSVVAQE.

In a further embodiment the tag has the sequence (SEQ ID NO: 42)
MKVIFLKDVKGKGKKGEIKDVADGYANNFLFKQGLAIEATPANIKA
LEAQKQKEQRQAAEELANAKKLKEELEKLTVEIPAKAGEGGRLFGS
ITSKQIAEALQAQHGLKLDKRKIELADAIRSLGYTNVPVKLHPEVT
ATLKVHVKEQK.

In a further embodiment the tag has the sequence (SEQ ID NO: 43)
MKVVLLKDVSKIGKKGEIKNVSDGYARNYLIPKGLALEATPRVLKR

LEAEKRKKEEEKIQ IKTQNEELLKMLKKFLYKIPVKAGESGKLFG

ALTNSDIAK AVEKIADVNI DKKFIVLEKPIKEIGMYDVLVRLPE

GVSGKIKVEVIQEGKN.

In a further embodiment the tag has the sequence (SEQ ID NO: 44)
MKLILTQEVAGLGGPGDVVEVRDGYGRNYLLPKRLAMPASPGAVKQ

VALIKRAREVREIRDLDQARALRDQLEALPVTLPARAGSGGRLFGS

VTPDDIAAAVHAAGGPKLDKRRIEISGPIKTIGSHQVTVRLHPEVS

ATVSVEVVPAS.

The tag may be attached directly to the N-terminal amino acid in the processing enzyme in question or via a linker group. Such linker group may have a multipurpose function i.e. to facilitate attachment of the tag to the processing enzyme and to position the tag and the processing enzyme relatively to each other to enable correct folding of the processing enzyme. The linker may also serve to present the tag in a favorable way to the purification matrix used for purification of the tagged processing enzyme.

The linker may have from 1-30, from 1-25, from 1-20, from 1-15, from 1-14, from 1-13, from 1-12, from 1-11, from 1-10, from 1-9, from 1-8, from 1-7, from 1-6, from 1-5 amino, from 1-4 or from 1-3 acid residues.

In a further embodiment the linker will have from 2-30, from 2-25, from 2-20, from 2-15, from 2-14, from 2-13, from 2-12, from 2-11, from 2-10, from 2-9, from 2-8, from 2-7, from 2-6, from 2-5 or from 2-4 amino acid residues.

In a further embodiment the linker will have from 3-30, from 3-25, from 3-20, from 3-15, from 3-14, from 3-13, from 3-12, from 3-11, from 3-10, from 3-9, from 3-8, from 3-7, from 3-6, from 3-5 or from 3-4 amino acid residues.

In a further embodiment the linker will have from 4-30, from 4-25, from 4-20, from 4-15, from 4-14, from 4-13, from 4-12, from 4-11, from 4-10, from 4-9, from 4-8, from 4-7, from 4-6 or from 4-5 amino acid residues.

In a further embodiment the linker will have from 5-30, from 5-25, from 5-20, from 5-15, from 5-14, from 5-13, from 5-12, from 5-11, from 5-10, from 5-9, from 5-8, from 5-7 or from 5-6 amino acid residues.

In a further embodiment the linker will have from 6-30, from 6-25, from 6-20, from 6-15, from 6-14, from 6-13, from 6-12, from 6-11, from 6-10, from 6-9, from 6-8 or from 6-7 amino acid residues.

In a further embodiment the linker will have from 7-30, from 7-25, from 7-20, from 7-15, from 7-14, from 7-13, from 7-12, from 7-11, from 7-10, from 7-9 or from 6-8 amino acid residues.

On one embodiment the linker has 20 amino acid residues.

In another embodiment the linker has 15 amino acid residues.

In another embodiment the linker has 12 amino acid residues.

In another embodiment the linker has 10 amino acid residues.

In another embodiment the linker has 9 amino acid residues.

In another embodiment the linker has 8 amino acid residues.

In another embodiment the linker has 7 amino acid residues.

In another embodiment the linker has 6 amino acid residues.

In another embodiment the linker has 5 amino acid residues.

The amino acid residues in the linker may be any amino acid residue and may be the same or different depending on the intended function of the linker.

In one embodiment the linker will comprise amino acid residues which render the linker a flexible structure such as alternating Ser and Gly residues. Other amino acid residues result in a rigid structure i.e. amino acids which may form alpha helical structures, such as Ala and Leu. Furthermore, certain amino acid residues add a structural bend to the linker e.g. Pro.

Non-limiting examples of linker groups are SSSGSSGSSGSS (SEQ ID NO:28), GGSSGGSS (SEQ ID NO:29), SSSGSGSG (SEQ ID NO:30), ALALALA (SEQ ID NO:31), ALALALAPA (SEQ ID NO:32), SSSALALALA (ID NO:33); SGSGSGSGS (ID NO:34), SSSGSGSGSG (SEQ ID NO:47) and GSSGSGS (SEQ ID NO:48).

In one embodiment the linker has the sequence SSSGSSGSSGSS (SEQ ID NO;28).

In another embodiment the linker has the sequence GGSSGGSS (SEQ ID NO:29).

In another embodiment the linker has the sequence SSSGSGSG (SEQ ID NO:30).

In another embodiment the linker has the sequence ALALALA (SEQ ID NO:31).

In another embodiment the linker has the sequence ALALALAPA (SEQ ID NO:32)

In another embodiment the linker has the sequence SSSALALALA (ID NO:33).

In another embodiment the linker has the sequence SGSGSGSGS (ID NO:34).

In another embodiment the linker has the sequence SSSGSGSGSG (SEQ ID NO:47).

In another embodiment the linker has the sequence GSSGSGS (SEQ ID NO:48).

In one embodiment the above described tags may be a combination of two tags which may be the same or different. Also the tag may be an analogue of the specifically disclosed tags. With an "analogue" is meant a sequence having up to 10% mutations compared to the original sequence. Such mutations will comprise additions, deletions or additions or any combination thereof as long as such mutations do not alter the original functionality of the tag.

In one embodiment the invention encompasses tagged processing enzymes wherein the tag is a truncated analogue of the original tag. The expression "truncated analogue" is meant to cover a sequence of the original tag wherein up to 10% of the original amino acid residues from either the N-terminal or the C-terminal end have been deleted provided that the truncated analogue has retained the functionality of the unmodified sequence.

If the tag comprises a combination of two tags these tags will in one embodiment be connected by a linker.

In one embodiment the linker connecting two tags are selected from the group consisting of SSSGSSGSSGSS (SEQ ID NO;28); GGSSGGSS (SEQ ID NO:29), SSSGSGSG (SEQ ID NO:30), ALALALA (SEQ ID NO:31), ALALALAPA (SEQ ID NO:32), SSSALALALA (ID NO:33); SGSGSGSGS (ID NO:34), SSSGSGSGSG (SEQ ID NO:47) and GSSGSGS (SEQ ID NO:48).

The invention will cover any combination of the embodiments of the tag, the linker and the processing enzyme as disclosed herein.

In one embodiment the tagged processing enzyme will comprise an N-terminal extension comprising a combination of the tag and the linker selected from the following group: SEQ ID NO:1 and SEQ ID NO:28, SEQ ID NO:3 and SEQ ID NO:28, SEQ ID NO:6 and SEQ ID NO:28, SEQ ID NO:9 and SEQ ID NO:28, SEQ ID NO:10 and SEQ ID NO:28, SEQ ID NO:11 and SEQ ID NO:28, SEQ ID NO:12 and SEQ ID NO:28, SEQ ID NO:13 and SEQ ID NO:28, SEQ ID NO:15 and SEQ ID NO:28, SEQ ID NO:16 and SEQ ID NO:28, SEQ ID NO:20 and SEQ ID NO:28, SEQ ID NO:21 and SEQ ID NO:28, SEQ ID NO:24 and SEQ ID NO:28, SEQ ID NO:27 and SEQ ID NO:28, SEQ ID NO:18 and SEQ ID NO:28, SEQ ID NO:19 and SEQ ID NO:28, SEQ ID NO:41 and SEQ ID NO:28, SEQ ID NO:42 and SEQ ID NO:28, SEQ ID NO:43 and SEQ ID NO:28, and SEQ ID NO:44 and SEQ ID NO:28, In one embodiment the tagged processing enzyme will comprise an N-terminal extension comprising a combination of the tag and the linker selected from the following group: SEQ ID NO:1 and SEQ ID NO:47, SEQ ID NO:3 and SEQ ID NO:47, SEQ ID NO:6 and SEQ ID NO:47, SEQ ID NO:9 and SEQ ID NO:47, SEQ ID NO:10 and SEQ ID NO:47, SEQ ID NO:11 and SEQ ID NO:47, SEQ ID NO:12 and SEQ ID NO:47, SEQ ID NO:13 and SEQ ID NO:47, SEQ ID NO:15 and SEQ ID NO:47, SEQ ID NO:16 and SEQ ID NO:47, SEQ ID NO:20 and SEQ ID NO:47, SEQ ID NO:21 and SEQ ID NO:47, SEQ ID NO:24 and SEQ ID NO:47, SEQ ID NO:27 and SEQ ID NO:47, SEQ ID NO:18 and SEQ ID NO:47, SEQ ID NO:19 and SEQ ID NO:47, SEQ ID NO:41 and SEQ ID NO:47, SEQ ID NO:42 and SEQ ID NO:47, SEQ ID NO:43 and SEQ ID NO:47 and SEQ ID NO:44 and SEQ ID NO:47.

In one embodiment the tagged processing enzyme will comprise an N-terminal extension comprising a combination of the tag and the linker selected from the following group: SEQ ID NO:1 and SEQ ID NO:48, SEQ ID NO:3 and SEQ ID NO:48, SEQ ID NO:6 and SEQ ID NO:48, SEQ ID NO:9 and SEQ ID NO:48, SEQ ID NO:10 and SEQ ID NO:48, SEQ ID NO:11 and SEQ ID NO:48, SEQ ID NO:12 and SEQ ID NO:48, SEQ ID NO:13 and SEQ ID NO:48, SEQ ID NO:15 and SEQ ID NO:48, SEQ ID NO:16 and SEQ ID NO:48, SEQ ID NO:20 and SEQ ID NO:48, SEQ ID NO:21 and SEQ ID NO:48, SEQ ID NO:24 and SEQ ID NO:48, SEQ ID NO:27 and SEQ ID NO:48, SEQ ID NO:18 and SEQ ID NO:48, SEQ ID NO:19 and SEQ ID NO:48, SEQ ID NO:41 and SEQ ID NO:48, SEQ ID NO:42 and SEQ ID NO:48, SEQ ID NO:43 and SEQ ID NO:48 and SEQ ID NO:44 and SEQ ID NO:48.

In on embodiment tag is selected from the group consisting of SEQ ID NO:10, SEQ ID NO:41, SEQ ID NO:42, SEQ ID NO:43 and SEQ ID NO:44 and the linker is selected from the group consisting of SEQ ID NO:28, SEQ ID NO:29, SEQ ID NO:30, SEQ ID NO:34, SEQ ID NO:47 and SEQ ID NO:48.

In another aspect the present invention is related to a method for making a tagged processing enzyme, which method comprises i) expression of a processing enzyme comprising an N-terminal tag according to any of the herein disclosed embodiments derived from a highly basic protein from a thermophilic bacteria in a suitable expression host, ii) loading the expressed tagged processing enzyme on a cation-exchange column, iii) and eluting the tagged processing enzyme with a suitable eluent.

In another aspect the invention is related to a method for modifying target protein precursors comprising the steps of reacting a tagged processing enzyme according to the invention with the target protein precursor and separating a target protein from the processing enzyme.

The processing enzymes are typically selected from oxidoreductases, transferases, hydrolases, lyases, isomerases and ligases.

In one embodiment the processing enzyme is a protease which is used to cleave fusion proteins.

In one embodiment the processing protease is selected from the group consisting of aspartic, metallo, serine and cysteine proteases.

In a further embodiment serine proteases include trypsins, chymotrypsins, enterokinase (EK), thrombin, factor Xa and kallikreins.

In one embodiment the cystein proteases are selected from the group of 3C proteases and 2A proteases encoded by the viral genomes of the group of Corona viridae, Picoma viridae, Retro viridae, Adeno viridae or Flavi viridae. Other preferred embodiments include 3C and 2A proteases from Picoma viridae and Corona viridae.

In a further embodiment the 3C proteases are selected from the Human Rhino Virus 3C protease with the sequence GPNTEFALSLLRKNIMTITTSKGEFT-GLGIHDRVCVIPTHAQPGDDV-LVNGQKIRVKDKYKLVDPENINLELTV-LTLDRNEKFRDIRGFISEDLEGVDATLVV HSNNFTNTILEVGPVTMAGLINLSSTPT-NRMIRYDYATKTGQCGGVLCATGKIFGIHVGGNG RQGFSAQLKKQYFVEKQ (SEQ ID NO: 35); Hepatitis A strain 18 3C protease with the sequence STLEIAGLVRKN-LVQFGVGEKNGCVRWVMNALGVKD-DWLLVPSHAYKFEKDYEMMEFYFNRG-GTYYSISAGNVVIQSLDVGFQDVVLMKVPTIPKFRD ITEHFIKKGDVPR ALNRLATLVTTVNGTPMLISEG-PLKMEEKATYVHKKNDGT-TVDLTVDQAWRGKGEGLPGM CGGALVSSNQSIQ-NAILGIHVAGGNSILVAKLVTQEMFQNIDKKIESQ (SEQ ID NO: 45) or Rabbit hemorrhagic disease virus 3C-like protease with the sequence

```
                                    (SEQ ID NO: 46)
GLPGFMRHNGSGWMIHIGNGLYISNTHTARSSCSEIVTCSPTTDLCL

VKGEAIRSVAQIAEGTPVCDWKKSPISTYGIKKTLSDSTKIDVLAYD

GCTQTTHGDCGLPLYDSSGKIVAIHTGKLLGFSKMCTLIDLTITKGV

YE.
```

In a further embodiment the protease is from a plant virus. The proteases will typically be from the following plant virus families: Bromoviridae, Partitiviridae, Geminiviridae, Potyviridae, Tombusviridae, Comoviridae, Rhabdoviridae, Reoviridae, Potyviridae, Sequiviridae and Bunyaviridae.

In one embodiment the protease from a plant virus is the mature Tobacco etch virus (TEV) protease with the amino acid sequence:

```
                                    (SEQ ID NO: 38)
GESLFKGPRDYNPISSTICHLTNESDGHTTSLYGIGFGPFIITNKHL

FRRNNGTLLVQSLHGVFKVKNTTTLQQHLIDGRDMIIRMPKDFPPF

PQKLKFREPQREERICLVTTNFQTKSMSSMVSDTSCTFPSSDGIFWK

HWIQTKDGQCGSPLVSTRDGFIVGIHSASNFTNTNNYFTSVPKNFME

LLTNQEAQQWVSGWRLNADSVLWGGHKVFMVKPEEPFQPVKEATQLM

N
```

The target protein which can be produced from a precursor protein modified by the processing enzyme according to the invention may be selected from human proteins and their analogues such as aprotinin, tissue factor pathway inhibitor or other protease inhibitors, insulin or insulin analogues, human or bovine growth hormone, interleukin, glucagon, GLP-1, GLP-2, IGF-I, IGF-II, tissue plasminogen activator, transforming growth factor α or β, platelet-derived growth factor, GRF (growth hormone releasing factor), immunoglubolines, EPO, TPA, protein C, blood coagulation factors such as FVII, FVIII, FIV and FXIII, exendin-3, exentidin-4, and enzymes or functional analogues thereof.

In a further aspect of the invention the target protein is selected from insulin antagonist or agonist peptides such as, S661 or peptide hormones such as amylin or functional analogues thereof.

In a further aspect of the invention the target protein is selected from enzymes relevant to any modification of proteins such as transglutaminases, transferases and racemases.

In one embodiment the invention is related to a process for removal of a prodomain from the protransglutaminase (proTGase) using a tagged processing enzyme according to the invention.

In another embodiment the invention is related to a process for cleavage of a protransglutaminase (proTGase) with a tagged HRV14 3C protease, a tagged HAV18 3C protease or a tagged RHDV 3C protease. In this embodiment the tag may be selected from SEQ ID NO:10, SEQ ID NO:41, SEQ ID NO:42, SEQ ID NO:43 or SEQ ID NO:44 and the linker may be selected from the group consisting of SEQ ID NO:28, SEQ ID NO:29, SEQ ID NO:30, SEQ ID NO:34, SEQ ID NO:47 and SEQ ID NO:48.

In another embodiment the invention is related to a process for removal of fusion partners of human growth hormone or analogues thereof with a tagged HRV14 3C protease, a tagged HAV18 3C protease, a tagged TEV protease or a tagged RHDV 3C protease. In this embodiment the tag may be selected from SEQ ID NO:10, SEQ ID NO:41, SEQ ID NO:42, SEQ ID NO:43 or SEQ ID NO:44 and the linker may be selected from the group consisting of SEQ ID NO:28, SEQ ID NO:29, SEQ ID NO:30, SEQ ID NO:34, SEQ ID NO:47 and SEQ ID NO:48.

In another embodiment the invention is related to a process for removal of fusion partners of human amylin or analogues thereof with a tagged HRV14 3C protease, a tagged HAV18 3C protease, a tagged TEV protease or a tagged RHDV 3C protease. In this embodiment the tag may be selected from SEQ ID NO:10, SEQ ID NO:41, SEQ ID NO:42, SEQ ID NO:43 or SEQ ID NO:44 and the linker may be selected from the group consisting of SEQ ID NO:28, SEQ ID NO:29, SEQ ID NO:30, SEQ ID NO:34, SEQ ID NO:47 and SEQ ID NO:48.

DESCRIPTION OF THE INVENTION

Figure 1:
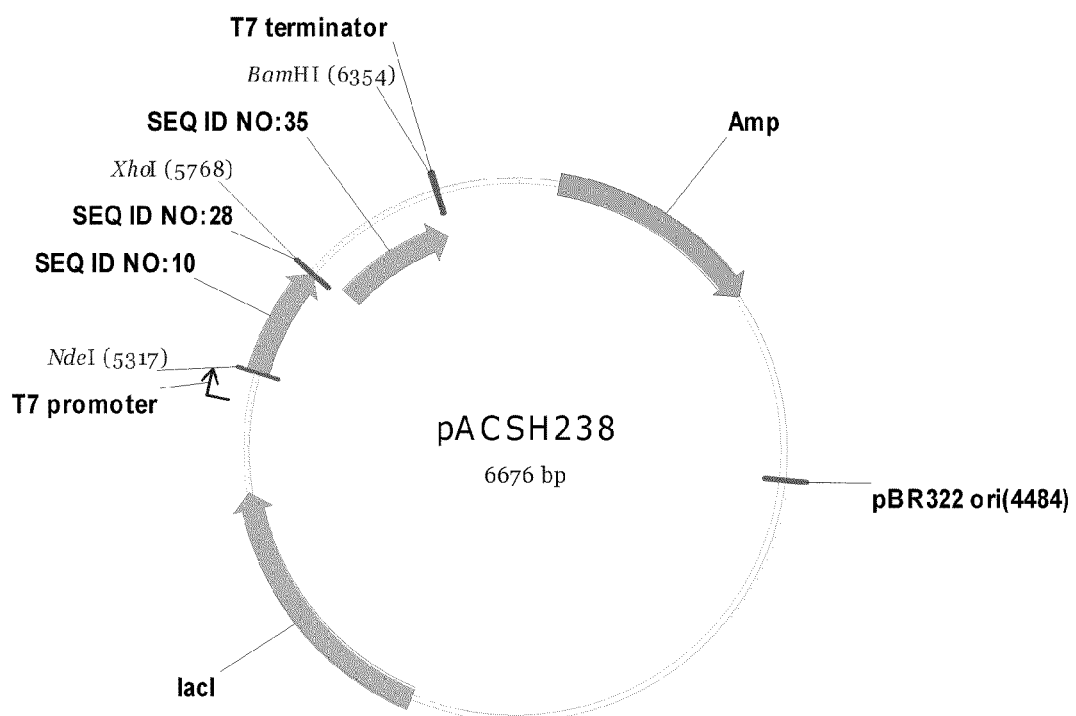
FIG. 1: discloses a vector map of the pET11a derived vector encoding the pACSH238 processing enzyme consisting of SEQ ID NO:10 as N-terminal purification tag, SEQ ID NO:28 as linker and SEQ ID NO:35 as the HRV14 3C protease. NdeI, XhoI and BamHI cloning sites are indicated as well lacI coding sequence, ampicillin (bla) coding sequence, pBR322 origin of replication, T7 promoter region, T7 terminator region and FIG. 2 discloses an extracted and deconvoluted mass spectrum of pACSH294 incubated with pACSH239 overnight at 25 degrees Celsius. At 1:100 enzyme to substrate ratio, the S661 peptide (4802.1 Da) is clearly detected as well as the released tag+linker (10168.4 Da). No intact fusion protein was detected, which indicates that the fusion protein was completely cleaved into to the tag part and the S661 peptide. Y-axis indicates intensity of ions measured. X-axis indicates molecular mass in Dalton (Da).

The present invention provides novel processing enzymes which can be used to modify proteins e.g. to cleave fusion proteins expressed in microbial host cells. Furthermore, the present invention provides a method for efficient expression and purification of such tagged processing enzymes.

The processing enzymes according to the present invention will comprise N-terminally fused tags that facilitate soluble expression of the tagged processing enzyme in high yields and enable an efficient purification using a single cation exchange chromatography step as well as easy removal of the tagged processing enzyme after use.

The tags will increase the solubility and hereby also the stability of the tagged processing enzyme. This is an advantage because poorly soluble enzymes require a greater reaction volume, incubation time and more specific reaction conditions.

The tags will also facilitate the binding to a cation column and thus enable on-column cleavage using cation exchange chromatography matrix as immobilizer for the tagged processing enzyme.

Some of the tags used according to the present invention are disclosed in copending application PCT/EP2006/061493.

These tags are derived from strains of thermophilic bacteria with optimum temperatures ranging from ~50° C. to above the boiling point of water. The strains that survive at extremely high temperatures are called hyperthermophiles or thermophiles and have a temperature optimum of 80° C. (176° F.) or higher. Thermophilic bacteria occur naturally in hot springs, hot soils, geothermal vents and other places were high temperature are present. Bacillus stearothermophillus from which RS21_BACST (SEQ ID NO:1) was cloned and used as a tag is for example found to grow above 65° C. in many soils. In order to survive the high temperatures, these organisms have evolved proteins which are more stable than those of mesophiles.

The tags according to the present invention derived from such thermophilic bacteria are in general soluble, highly stable and have a very basic pI due to a large amount of Arg and Lys residues present in the amino acid sequence. The pI of the tags will generally be between 9 and 13.5.In one embodiment the tag has a pI above about 9. In another embodiment the tag has a pI above between about 9 and 12.5. In another embodiment the pI of the tag will be between about 10 and about 12.5 and in a further aspect the pI is about 10.

The solubility is believed to be derived from the generally high surface charge of the proteins.

The processing enzymes according to the present invention may be used to process recombinantly expressed proteins to give a desired modified protein.

The processing enzymes are selected from the following group of enzymes: oxidoreductases, which may catalyze oxidation/reduction reactions, transferases, which may transfer a functional group (eg. phosphate groups), hydrolases which catalyze the hydrolysis of various bonds (including proteases which hydrolyse peptide bonds), lyases, which cleave bonds by means other than hydrolysis and oxidation, isomerase, which catalyze changes within a single molecule, or ligase, which join two molecules through covalent bonds.

These enzymes may either be wildtype enzymes or variants or analogues thereof modified by well known mutagenesis steps.

Examples of tagged proteases that can be used for cleavage of fusion partners from a target protein or removal of pro-domains or trimming of amino acids in the N-terminal or C-terminal of target proteins are aspartic, metallo, serine and cysteine proteases.

Non-limiting examples of serine proteases include trypsins, chymotrypsins, enterokinase (EK), thrombin, factor Xa and kallikreins.

Non-limiting examples of cysteine proteases include viral proteases obtained from the group of Corona viridae, Picorna viridae, Retro viridae, Adeno viridae, Calici viridae or Flavi viridae. Further examples include proteases from herpes virus, cytomegalo virus, hepatitis A-D virus, dengue virus, rhino virus, polio virus, coxsackie virus, servere acute respiratory syndrome virus (SARS), mengo virus, polio virus, footh and mouth disease virus, human immune deficiency virus (HIV), human T-lymphotrophic virus (HTLV), human foamy virus and adenovirus. Other non-limiting examples includes cysteine proteases derived from bacteria such as *Leishmania* sp. or eukaryotic microbes such as *Trypanosoma* sp.

In one embodiment the cysteine proteases are selected from the group of 3C proteases and 2A proteases encoded by the viral genomes of the group of Corona viridae, Picorna viridae, Retro viridae, Adeno viridae or Flavi viridae. Other preferred embodiments include 3C and 2A proteases from Picorna viridae and Corona viridae. Other examples of cysteine proteases include caspases such as human caspases 1-10.

A review of 3C proteases is found in Krausslich, H. G. & Wimmer, E., Viral proteinases, Annual Review of Biochemistry (1988) 57, 701-754.

Non-limiting examples of metallo proteases include matrix metallo proteases such as matrixins or membrane bound metallo proteases such as MT1-MMP.

Other embodiments includes aspartic proteases such as pepsin and cathepsin e.g. cathepsin D and chymosin.

Other examples of enzymes include lipases, phospatases, glycosyl hydrolases (eg. mannosidases, xylosidases, fucosidases), kinases, mono or dioxidases, peroxidases, transaminases, carboxypeptidases, amidases, esterases and phosphatases.

The target protein precursor which can be modified by the tagged processing enzyme may be any protein and illustrative examples are aprotinin, tissue factor pathway inhibitor or other protease inhibitors, insulin or insulin precursors, human or bovine growth hormone, interleukin, glucagon, GLP-1, GLP-2, IGF-I, IGF-II, tissue plasminogen activator, transforming growth factor α or β, platelet-derived growth factor, GRF (growth hormone releasing factor), immunoglubolines, EPO, TPA, protein C, blood coagulation factors such as FVII, FVIII, FIV and FXIII, exendin-3, exentidin-4, and enzymes or functional analogues thereof.

Other examples of target proteins are transforming growth factor α (TGF-α), transforming growth factor β (TGF-β), epidermal growth factor (EGF), vascular endothelial growth factor (VEGF), thrombopoietin (TPO), interferon, pro-urokinase, urokinase, plasminogen activator inhibitor 1, plasminogen activator inhibitor 2, von Willebrandt factor, a cytokine, e.g. an interleukin such as interleukin (IL) 1, IL-1Ra, IL-2, IL-4, IL-5, IL-6, IL-9, IL-11, IL-12, IL-13, IL-15, IL-16, IL-17, IL-18, IL-20, IL-21 IL-21,IL-22,IL-23,IL-24, IL-25, IL-26, IL-27, IL-28,IL-29,IL-30, IL-31, IL-32 or IL-33, a colony stimulating factor (CFS) such as GM-CSF, stem cell factor, a tumor necrosis factor such as TNF-α, lymphotoxin-α, lymphotoxin-β, CD40L, or CD30L, a protease inhibitor e.g. aprotinin, an enzyme such as superoxide dismutase, asparaginase, arginase, arginine deaminase, adenosine deaminase, ribonuclease, catalase, uricase, bilirubin oxidase, trypsin, papain, alkaline phosphatase, β-glucoronidase, purine nucleoside phosphorylase or batroxobin, an opioid, e.g. endorphins, enkephalins or non-natural opioids, a hormone or neuropeptide, e.g. calcitonin, glucagon, gastrins, adrenocorticotropic hormone (ACTH), cholecystokinins, lutenizing hormone, gonadotropin-releasing hormone, chorionic gonadotropin, corticotrophin-releasing factor, vasopressin, oxytocin, antidiuretic hormones, thyroid-stimulating hormone, thyrotropin-releasing hormone, relaxin, prolactin, peptide YY, neuropeptide Y, pancreastic polypeptide, leptin, CART (cocaine and amphetamine regulated transcript), a CART related peptide, perilipin, melanocortins (melanocyte-stimulating hormones) such as MC-4, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor and melanotonins.

In another embodiment of the invention the target protein may be insulin receptor agonist or antagonist peptides or other peptides designed to interact with other cell membrane receptors.

One embodiment of the present invention will include co-expression of the tagged processing enzyme according to the invention and the target protein precursor thus facilitating in vivo processing of the target protein precursor and easy removal of the processing enzyme during initial purification steps.

The expressed tagged processing enzyme produced by the method according to the invention may be recovered from the culture medium by conventional procedures including separating the host cells from the medium by centrifugation or filtration, releasing the tagged processing enzyme by mechanical cell disruption, such as ultrasonication or pressure, precipitating the proteineous components of the supernatant or filtrate by means of a salt, e.g. ammonium sulphate.

Any suitable cation exchange matrix available from commercial suppliers can be used in the method according to the invention and a non limiting list of suitable cation exchange column material is: SP Sepharose Fast Flow, SP Sepharose XL; Streamline SP XL, Streamline Direct CST, Obelix SP, S-Support Unosphere, SP Sepharose High Performance, Source30S and Toyopearl SP650S TosoHaas.

The steps following the processing step e.g. cleavage of a fusion protein may include a cation exchange column purification as in the first step. Purification steps following cleavage may also comprise other means of purification such as anion exchange chromatography, hydrophobic interaction chromatography and gel filtration chromatography (see, for example, Scopes, R., Protein Purification, Springer-Verlag, N.Y., 1982).

The nucleic acid construct encoding the tagged processing enzyme according to the invention may suitably be of genomic or cDNA origin, for instance obtained by preparing a genomic or cDNA library and screening for DNA sequences coding for all or part of the fusion protein by hybridization using synthetic oligonucleotide probes in accordance with standard techniques (cf. Sambrook et al., Molecular Cloning: A Laboratory Manual, 2nd. Ed. Cold Spring Harbor Laboratory, Cold Spring Harbor, N.Y., 1989).

The nucleic acid construct encoding the tagged processing enzyme may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e.g. in an automatic DNA synthesiser, purified, annealed, ligated and cloned in suitable vectors. The DNA sequences encoding the fusion protein may also be prepared by polymerase chain reaction such as splicing by overlap extension PCR using specific primers, for instance as described in U.S. Pat. No. 4,683,202, Saiki et al., Science 239 (1988), 487 - 491, or Sambrook et al., supra.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The DNA sequences encoding the tagged processing enzyme are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the tagged processing enzyme is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the fusion protein.

Expression vectors for use in expressing the tagged processing enzyme will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylosidase gene, or the phage Lambda $P_R$ or $P_L$ promoters or promoters used for expression in *E. coli* eg. lac, trp, phoA, araBAD, tac, bacteriophage T7 and cspA.

The vector may also comprise a selectable marker, e.g. a gene product which complements a defect in the host cell, such as the gene coding for dihydrofolate reductase (DHFR) or a marker gene which confers resistance to a drug, e.g. ampicillin, kanamycin, tetracyclin, chloramphenicol, neomycin, hygromycin or methotrexate.

The DNA sequences encoding the tagged processing enzyme may also, if necessary, be operably connected to a suitable terminator, such as the human growth hormone terminator (Palmiter et al., Science 222, 1983, pp. 809-814) or the TPI1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the fusion polypeptide sequence itself. Such RNA splice sites may be obtained from adenovirus and/or immunoglobulin genes. Also contained in the expression vectors is a polyadenylation signal located downstream of the insertion site. Examples of polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9:3719-3730, 1981). The expression vectors may also include a non coding viral leader sequence, such as the adenovirus 2 tripartite leader, located between the promoter and the RNA splice sites; and enhancer sequences, such as the SV40 enhancer.

The host cell into which the DNA construct encoding the tagged processing enzyme is introduced may be any bacteria cell which is capable of producing the tagged processing enzyme.

Examples of bacterial host cells are grampositive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of *Streptomyces*, such as *S. lividans* or *S. murinus*, or gram-negative bacteria such as strains of *Escherichia coli*. The transformation of the bacteria may be effected by protoplast transformation or by using competent cells in a manner known per se (cf. Sambrook et al., supra).

When expressing protein in bacteria such as *E. coli*, the protein may be retained in the cytoplasm, typically as insoluble granules (known as inclusion bodies), or may be directed to the periplasmic space by a bacterial secretion sequence. In the former case, the cells are lysed and the granules are recovered and denatured after which the polypeptide is refolded by diluting the denaturing agent. In the latter case, the target protein may be cloned with a strong signal peptide sequence such as phoA, degQ, degS, degP, OmpA, OmpF, OmpH, OmpP, OmpT, lamb or pelB (from *Erwania carotovora*) and the polypeptide may be recovered from the periplasmic space by disrupting the cells, e.g. by sonication or osmotic shock, to release the contents of the periplasmic space and recovering the polypeptide.

The transformed or transfected host cell is then cultured in a suitable nutrient medium under conditions permitting expression of the tagged processing enzyme after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

"Application" means a sample containing the fusion protein which is loaded on a purification column.

"Flow through" means the part of the application containing host cell proteins and contaminants which do not bind to the purification column.

"Main peak" refers to the peak in a purification chromatogram which has the highest UV intensity and which contains the fusion protein.

"mAU" is milliabsorbance units.

"UV 280 intensity" is the absorbance at a wavelength of 280 nm at which proteins will absorb, measured in milliabsorbance units.

"UV214" is the absorbance at a wavelength of 214 nm at which proteins will absorb, measured in milliabsorbance units.

"IPTG" is isopropyl-β-D-thiogalactopyranoside.
"TIC" is Total Ion Count.
"HPLC" is high performance liquid chromatography.
The expression "protein" will cover both peptides and polypeptides.

A "target protein precursor" is a protein which is a precursor for the target protein and which must be processed by the processing enzyme to obtain the target protein. Examples includes fusion protein from which the fusion partner has to be removed by a processing enzyme to obtain the target protein, proteins from which post translational modifications (eg. glycosylations) have to be removed by a processing enzyme to obtain the target protein or proteins to which post translational modifications have to be added by a processing enzyme or combinations of the above.

A "target protein" is a protein which has been processed by a processing enzyme to reach it's intended form.

"SOE PCR" means Splicing by overlap extension PCR.

"LC-MS" refers to liquid chromatography mass spectrometry.

"% Solubility" is defined as the amount of soluble protein from host cell lysate divided by amount of soluble+insoluble fusion protein from host cell lysate×100.

"% Purity" is defined as the amount of the protein of interest divided by the amount of protein of interest+the amount of host cell contaminants×100.

SDS-PAGE is sodium dodecyl sulfate polyacrylamide gel electrophoreses.

In the present context the three-letter or one-letter indications of the amino acids have been used in their conventional meaning as indicated in table 1. Unless indicated explicitly, the amino acids mentioned herein are L-amino acids. Further, the left and right ends of an amino acid sequence of a peptide are, respectively, the N- and C-termini unless otherwise specified.

TABLE 1

Abbreviations for amino acids:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Example 1

Synthesis of a HRV14 3C Protease Encoding Sequence Using Overlap PCR

The amino acid sequence of the mature Human Rhino Virus strain 14 (HRV14) 3C protease is as follows:

(SEQ ID NO: 35)
GPNTEFALSLLRKNIMTITTSKGEFTGLGIHDRVCVIPTHAQPGDD

VLVNGQKIRVKDKYKLVDPENINLELTVLTDRNEKFRDIRGFISED

LEGVDATLVVHSSNNFTNTILEVGPVTMAGLINLSSTPTNRMIRYD

YATKTGQCGGVLCATGKIFGIHVGGNGRQGFSAQLKKQYFVEKQ

A DNA sequence encoding SEQ ID NO: 35 and codon optimized for expression in *E. coli* was generated. The mature HRV14 3C protease synthetic gene fragment was obtained by using splicing by overlap extension PCR methodology using two consecutive steps of PCR. In the first PCR reaction, 16 overlapping primers (eight forward and eight reverse primers) were used to generate the entire HRV14 sequence, including a 5-end region encoding a flexible linker (SEQ ID NO:28). Primers were ~50 bp of size and the overlap between primers was ~20 bp. In the second PCR reaction, terminal forward and reverse primers comprising XhoI and BamHI cloning sites, respectively, were used to amplify the whole sequence using the product of the first PCR reaction as a template. The Phusion PCR system (Finnzymes) was used. The first PCR reaction was setup as follows with suitable amounts of all 16 primers essentially according to the manufactures instructions. The PCR condition for the first reaction was as follows;

98° C. 30 sec (initial denaturation)
98° C. 10 sec(denaturation)
50° C. 30 sec (annealing)
72° C. 15 sec (elongation) for 10 cycles
72° C. 5 min (final elongation)

The PCR product from the first reaction was purified directly from the PCR solution using the GFX™ PCR DNA and Gel Band Purification Kit (GE Health care).

In the second PCR reaction, the most terminal forward and reverse primers were used to amplify the entire HRV14 3C encoding sequence from the PCR product from the first reaction. The conditions were the same as described for the first reaction, except that 55° C. were used as annealing temperature and 20 cycles were used instead of 10.

The PCR product from the second reaction has a size of ~600 base pairs as expected, judged by agarose gel electrophoresis. The PCR band was excised from agarose gels and the PCR product was purified using the GFX™ PCR DNA and Gel Band Purification Kit (GE Healthcare) according to the manufacturer's instructions. The purified PCR product was subcloned into plasmids using established TOPO cloning systems (Invitrogen) according to the manufacturer's instructions and ligation products were transformed into TOP10 *E. coli* cells (Invitrogen) for plasmid probagation. The correct sequence of XhoI/BamHI inserts of plasmids obtained from isolated TOP10 clones was verified by DNA sequencing.

Ligation of the HRV14 Sequence with Different Thermostable Alkaline Protein Tags into pET11a Vectors The XhoI/BamHI fragment comprising the HRV14 3C protease encoding region was excised from TOPO plasmids vectors (Invitrogen). XhoI/BamHI fragments were then ligated into pET11a vectors (Novagen) so that inserts encoding different N-terminal thermostable alkaline tags were linked to the 5-end of the linker and protease encoding region. Sixteen pET11a vectors encoding different tags fused to the N-terminal of the HRV14 3C protease with an intervening linker was generated as exemplified in FIG. 1.

Verification of the DNA sequence was performed by restriction enzyme cleavage and/or DNA sequencing.

The following tagged enzymes were produced:

| Product name | Tag | Linker | Processing enzyme |
|---|---|---|---|
| pACSH240 | SEQ ID NO: 1 | SEQ ID NO: 28 | SEQ ID NO: 35 |
| pACSH329 | SEQ ID NO: 3 | SEQ ID NO: 28 | SEQ ID NO: 35 |
| pACSH319 | SEQ ID: NO: 6 | SEQ ID NO: 28 | SEQ ID NO: 35 |
| pACSH320 | SEQ ID NO: 8 | SEQ ID NO: 28 | SEQ ID NO: 35 |
| pACSH321 | SEQ ID NO: 9 | SEQ ID NO: 28 | SEQ ID NO: 35 |
| pACSH238 | SEQ ID NO: 10 | SEQ ID NO: 28 | SEQ ID NO: 35 |
| pACSH322 | SEQ ID NO: 11 | SEQ ID NO: 28 | SEQ ID NO: 35 |
| pACSH323 | SEQ ID NO: 12 | SEQ ID NO: 28 | SEQ ID NO: 35 |
| pACSH324 | SEQ ID NO: 13 | SEQ ID NO: 28 | SEQ ID NO: 35 |
| pACSH325 | SEQ ID NO: 15 | SEQ ID NO: 28 | SEQ ID NO: 35 |
| pACSH326 | SEQ ID NO: 16 | SEQ ID NO: 28 | SEQ ID NO: 35 |
| pACSH239 | SEQ ID NO: 19 | SEQ ID NO: 28 | SEQ ID NO: 35 |
| pACSH327 | SEQ ID NO: 20 | SEQ ID NO: 28 | SEQ ID NO: 35 |
| pACSH328 | SEQ IDNO: 21 | SEQ ID NO: 28 | SEQ ID NO: 35 |
| pACSH331 | SEQ ID NO: 24 | SEQ ID NO: 28 | SEQ ID NO: 35 |
| pACSH332 | SEQ ID NO: 27 | SEQ ID NO: 28 | SEQ ID NO: 35 |

Expression of Tagged HRV14 3C Proteases.

pET 11 a vector construct encoding the HRV14 3C protease with different N-terminal tags were transformed into the Rosetta (DE3)(Novagen) *E. coli* strain by means of heat shock or chemical based standard methods. Transformed cells were probagated on LB (Luria-Bertani) medium agar plates containing 150 micrograms per milliter Ampicillin and 34 micrograms per milliter chloramphinicol overnight. Liquid LB medium with ampecillin and chloramphinicol was inoculated from culture plates and cultivated in shaker flasks at 37 degrees C. and 240 rpm. The temperature was lowered to 30 degrees C. when $OD_{600}$: ~0.4-0.8 was reached. 20-30 minutes after protein induction was initiated by adding 0.5 mM IPTG to the culture medium. The final $OD_{600}$ obtained after 3 hours induction was in range of 1.6-2.8. Cells were harvested by centrifugation. SDS-PAGE of lysates of pellets containing induced and uninduced cells, as well as soluble and insoluble fractions of induced cells (obtained by ultrasonication and centrifugation in a buffer consisting of 25 mM $NaPO_4$ pH 7) was performed to evaluate expression level and solubility of the HRV14 3C protease variants. Although differences were observed in expression levels, a very high solubility (~80% or more) was observed for most tagged versions of the HRV14 3C protease.

Purification of HRV14 3C Protease N-Terminally Tagged with SEQ ID NO:19(pACSH239):

Cell culture pellets (from 40 ml of culture) of the pACSH239 protease were disrupted by ultrasonication in a buffer containing 25 mM $NaPO_4$ pH 7. Cell debris was spun down by centrifugation at 10.000 g. Supernatants were sterilefiltrated before purification, which was carried out using a AKTA explorer 100 purification system (GE Healthcare). A prepacked SP Sepharose FF HiTrap column with a 5 ml column volume (GE Healthcare) was used for the separation at a flow rate of 3 ml/min using the following buffers:

Buffer A: 50 mM sodium phosphate, pH 7+1 mM EDTA
Buffer B: 50 mM sodium phosphate, pH 7+1M NaCl+1 mM EDTA The column was initially equilibrated for 7 column volumes of buffer A. After loading of the application, unbound protein was removed by washing using 7 column volumes of buffer A. A linear gradient from 0-100% buffer B for 20 column volumes was used to elute the pACSH239 protease from the column. The fusion protein was eluted from the column at a salt concentration of 0.4-0.5 M NaCl. Some protein was lost in the flow through. However, the pACSH239 protease could be purified to high purity (~85-90%) as determined by HPLC and SDS-PAGE standard methods in a single cation exchange chromatographic step. By LC-MS it was also verified that the eluted pACSH239 protease had a molecular weight as expected.

Purification of HRV14 3C Protease N-Terminally Tagged with SEQ ID NO:10(pACSH238)

Supernatants ready for purification were prepared from cell culture pellets sonicated in 25 mM $NaPO_4$ pH 7, from 80 ml of cell culture as described for pACSH239. A SP Sepharose FF prepacked 5 ml HiTrap column (GE Healthcare) was loaded with the application. The flow rate was 3 ml/min and the buffers used for the purification was:

Buffer A: 50 mM sodium phosphate, pH 7
Buffer B: 50 mM sodium phosphate, pH 7+1M NaCl The column was initially equilibrated for 7 column volumes with buffer A. Unbound sample was removed in a washing step using 7 column volumes of Buffer A and the pACSH238 protease was eluted from the column using linear gradient from 0-100% buffer B for 20 column volumes.

The pACSH238 protease was eluted from the column at a concentration of ~0.2 M NaCl. In contrast to the pACSH239 protease, the major part of the pACSH238 protease bond to the column at these purification conditions. By LC-MS it was also verified that the eluted protease had a molecular weight as expected. The recovery was 4 times higher after the first purification step compared to the pACSH239 protease and the purity was ~90% as judged from HPLC and SDS PAGE analysis.

Evaluation of the Activity of SEQ ID NO:19 Tagged HRV14 3C Protease (pACSH239)

The activity of pACSH239 protease was estimated using different amounts of the protease to cleave a fusion protein (pACSH294) comprising the S661 insulin receptor antagonist peptide with a N-terminal tag (SEQ ID NO: 19) and an intervening linker with a modified HRV14 3C cleavage site SSSGGSEVLFQ (SEQ ID NO: 36)

The S661 peptide has the following sequence:

(SEQ ID NO: 37)
GSLDESFYDWFERQLGGGSGGSSLEEEWAQIQCEVWGRGCPSY.

Figure 2:
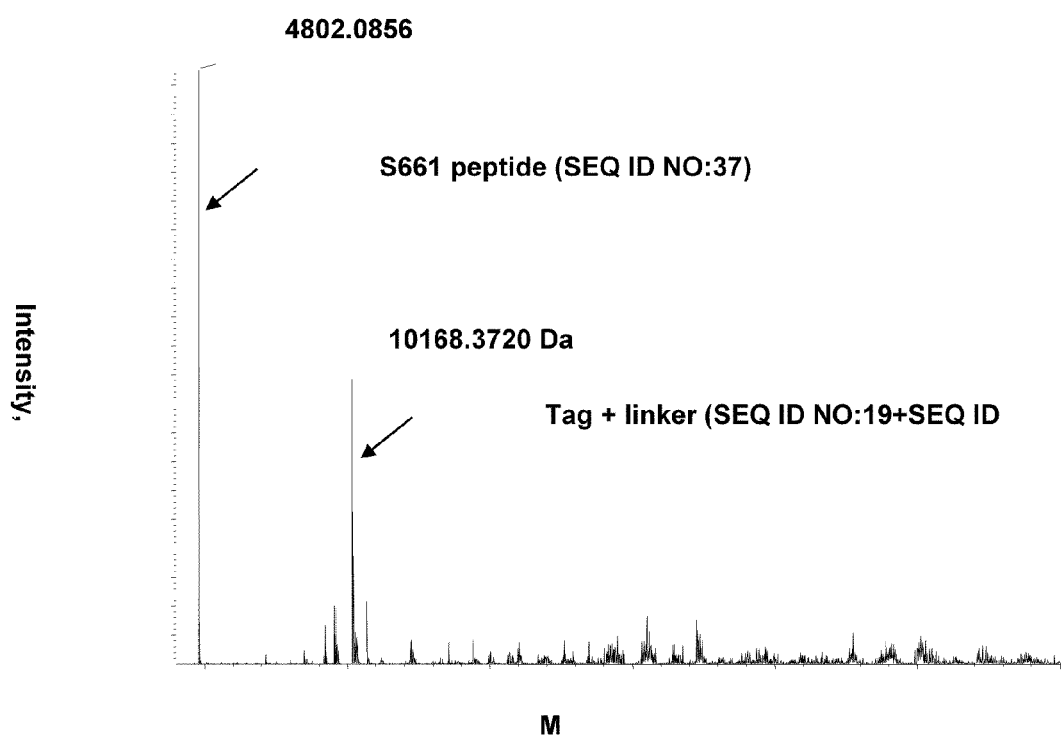

Comparable protein concentrations of the pACSH294 fusion protein substrate and the pACSH239 protease were calculated by integration of UV214 nm absorbance peak areas from analysis of HPLC chromatograms. Enzyme and substrate were mixed in a 200 uL reaction volume and incubated 6 or 12 hours at 25° C. in a cleavage buffer containing 50 mM Tris HCl pH 7.5, 150 mM NaCl using different enzyme to substrate ratios (adjusted according to concentration). LC-MS studies showed that only the S661 peptide(SEQ ID NO: 37) and the released tag (SEQ ID NO: 19)+linker (SEQ ID NO: 36) was observed after 12 hours incubation using 1:100 enzyme to substrate ratio (FIG. 2). Only very small amounts of fusion protein were left after 12 hours using a 1:200 ratio. The results therefore indicate that an enzyme/substrate ratio of 1:100-1:200 is sufficient for complete processing of the pACSH294 fusion protein during a overnight incubation.

The released S661 peptide, present in the digest, could subsequently be purified to more than 98% purity using an anion exchange chromatography column (HiTrap Q sepharose High Performance, 1 ml, GE Healthcare). Buffers and general purification conditions were as described for the purification of the pACSH239 protease. Whereas the S661 peptide bound this column, the pACSH239 protease was not eluted at any salt concentration from the column within the elution gradient, but could only be observed in the flow through as judged by LC-MS analysis of flow through fractions. Thus, the pACSH239 protease was efficiently removed from the target protein in the second purification step.

Evaluation of the Activity of SEQ ID NO:10 Tagged HRV14 3C Protease (pACSH238)

Identical amounts of pACSH238 or pACSH239 protease were used to process the pACSH294 substrate in a buffer consisting of 50 mM Tris HCl pH 7.5, 150 mM NaCl in a parallel experiment. Enzyme to substrate ratios of 1:25 or 1:50 were evaluated for the two enzymes. The amount of S661 insulin receptor antagonist peptide released from the pACSH294 fusion protein after 3 hours incubation at 30° C. was exactly the same for the two enzymes indicating that they have the same specific activity despite different sized tags attached to the N-terminal. As with the pACSH239 protease, the pACSH238 protease did not bind anion exchange column thus indicating that it can be efficiently removed by a suitable purification step following digestion of the target protein precursor.

Example 2

Cloning of Tagged Tobacco Etch Virus Proteases

The mature Tobacco etch virus (TEV) protease has the following amino acid sequence:

```
                                            (SEQ ID NO: 38)
GESLFKGPRDYNPISSTICHLTNESDGHTTSLYGIGFGPFIITNKH

LFRRNNGTLLVQSLHGVFKVKNTTTLQQHLIDGRDMIIIRMPKDFP

PFPQKLKFREPQREERICLVTTNFQTKSMSSMVSDTSCTFPSSDGI

FWKHWIQTKDGQCGSPLVSTRDGFIVGIHSASNFTNTNNYFTSVPK

NFMELLTNQEAQQWVSGWRLNADSVLWGGHKVFMVKPEEPFQPVKE

ATQLMN
```

An insert comprising the TEV sequence with a stabilizing mutation (S219V) was obtained by standard PCR methodology using the Phusion PCR system (Finnzymes), forward and reverse primers comprising XhoI and BamHI cloning site respectively and an existing TEV (Ser219Val) encoding plasmid as template. The 5'-end of the PCR product comprised a sequence encoding a flexible linker (SEQ ID NO: 28).

The PCR product was GFX purified (GE Healthcare) and subcloned in TOPO vectors according the manufacturers (Invitrogen) instructions and as described in Example 1. The correct TEV encoding sequence of XhoI/BamHI inserts from TOPO plasmids was verified by DNA sequencing. Correct inserts were excised from TOPO plasmids with XhoI/BamHI enzymes and fused to the 3'-end of inserts encoding thermostable alkaline tags into pET11a (Novagen) expression vectors. The following constructs were generated:

| Product name | Tag | Linker | Processing enzyme |
|---|---|---|---|
| pACSH307 | SEQ ID NO: 10 | SEQ ID NO: 28 | SEQ ID NO: 38 |
| pACSH308 | SEQ ID NO: 18 | SEQ ID NO: 28 | SEQ ID NO: 38 |
| pACSH309 | SEQ ID: NO: 19 | SEQ ID NO: 28 | SEQ ID NO: 38 |

Expression of Tagged TEV Protease Variants.

pACSH307, pACSH308 and pACSH309 protease encoding plasmids were transformed into the Rosetta (DE3) (Novagen) E. coli strains. Transformed cells were probagated on LB (Luria-Bertani) medium agar plates containing 150 micrograms per milliter Ampicillin and 34 micrograms per mL chloramphinicol overnight. Liquid LB medium with ampecillin and chloramphinicol was inoculated from culture plates and cultivated in shaker flasks at 37 degrees C. and 240 rpm. The temperature was lowered to 30° C. when $OD_{600}$: ~0.4-0.5 was reached. After 30 minutes adaption to this temperature, protein induction was initiated by adding 0.5 mM IPTG to the culture medium. The final $OD_{600}$ obtained after 3 hours induction was in range of 1.6. Cells were harvested by centrifugation. SDS-PAGE of lysates of pellets containing induced and uninduced cells, as well as soluble and insoluble fractions of induced cells (obtained by ultrasonication and centrifugation in a buffer consisting of 10 mM NaPO4 pH 7) was performed to evaluate expression level and solubility of the TEV protease variants. The expression levels were similar for all three constructs. The solubility was estimated to be highest for the SEQ ID NO: 10 tagged TEV variant (~70%) (pACSH307).

Purification of pACSH307 Protease

Purification the pACSH307 protease from sterile filtrated supernatants from culture pellets (from 80 ml culture) sonicated in 25 mM NaPO4 pH 7 was carried out using the AKTA Explorer 100 system (GE Healthcare) with exactly the conditions and buffers described for pACSH238 in Example 1. When separation was performed on HiTrap SP Sepharose FF 5 ml column, a peak was clearly eluted at about 0.25 M NaCl. LC-MS analysis of the fraction from the highest point of the peak gave a molecular mass exactly as expected for this construct and the purity of the main peak was ~85-90% as judged by SDS-PAGE and HPLC analysis Evaluation of the Activity of SEQ ID NO:10 Tagged TEV Protease (pACSH307)

The activity of pACSH307 protease was estimated using different amounts of the protease to cleave a fusion protein (pACSH248) comprising S661 insulin antagonist peptide (SEQ ID NO: 37), as described in example 1 with the same N-terminal tag (SEQ ID NO: 19), but with a linker comprising a Tobacco etch virus cleavage recognition site SSSGGSENLYFQ (SEQ ID NO:39). Digestion experiments were performed in a cleavage buffer containing 50 mM Tris HCl pH 8, 0.5 mM EDTA. LC-MS studies showed that after incubation for 8 hours with an enzyme to substrate ration of 1:1, the major part of the S661 peptide was released from the pACSH248 fusion protein. This verify that the tagged TEV protease is expressed and purified as an active enzyme and can be used to remove the SEQ ID NO:19 tag from the pACSH248 fusion protein.

Example 3

Cloning and Expression of proTGase.

The transglutaminase (tGASE) gene consists of a signal peptide and a prodomain followed by the mature tGASE sequence. A protGASE (without signal peptide, but with a N-terminal Met residue) was prepared by PCR from genomic DNA of *Streptomyces mobaraensis* using standard methodology. The prodomain was altered, so that a HRV14 3C cleavage site was included just before a Gly53-Pro54 N-terminal extension of the mature tGASE sequence. The protGASE sequence was cloned into the pET11a vector (pNNC130) using standard cloning techniques and the protein encoded by this plasmid had the following sequence (the mature tGASE sequence starts with residue 55):

```
                                           (SEQ ID NO: 40)
MDNGAGEETKSYAETYRLTADDVANINALNESAPAASSAGPSFRAP

LEVLFQGPDSDDRVTPPAEPLDRMPDPYRPSYGRAETVVNNYIRKW

QQVYSHRDGRKQQMTEEQREWLSYGCVGVTWVNSGQYPTNRLAFAS

FDEDRFKNELKNGRPRSGETRAEFEGRVAKESFDEEKGFQRAREVA

SVMNRALENAHDESAYLDNLKKELANGNDALRNEDARSPFYSALRN

TPSFKERNGGNHDPSRMKAVIYSKHFWSGQDRSSSADKRKYGDPDA

FRPAPGTGLVDMSRDRNIPRSPTSPGEGFVNFDYGWFGAQTEADAD

KTVWTHGNHYHAPNGSLGAMHVYESKFRNWSEGYSDFDRGAYVITF

IPKSWNTAPDKVKQGWP.
```

The pNNC130 plasmid was transformed into BL21 (DE3) (Novagen) and cultivated overnight on LB medium containing 150 micrograms per milliliter Ampecillin. Liquid LB medium containing Ampecillin was inoculated from overnight culture agar plates and cultivated at 37° C. at 240 rpm until $OD_{600}$ reach ~0.8. After 20 min. adaptation to 30° C., expression was induced with 0.1 mM IPTG. The cells were harvested after 4 hours of protein induction at a final $OD_{600}$ of approximately 2. SDS-PAGE analysis showed that the majority of protGASE was found in the soluble fraction in supernatants obtained after sonication in a buffer containing 10 mM $NaPO_4$ pH 8 and centrifugation of cell debris.

Purification of protGASE:

Cell pellets from 200 ml induced cell culture was dissolved in 40 ml 10 mM $NaPO_4$ buffer pH 8. Following sonication and centrifugation at 10.000 g, supernatants were sterile filtrated and the final application volume was adjusted to 50 ml with 10 mM $NaPO_4$ buffer pH 8.

The purification was performed using the instrumentation described in Example 1 and 2 using a flow rate of 3 ml/min and the following buffers:

Buffer A: 25 mM $NaPO_4$ buffer pH 8.0

Buffer B: 25 mM $NaPO_4$ buffer pH8.0, 0.5M NaCl

A 5 ml Q Sepharose High Performance (HP) HiTrap column (GE Healthcare) was equilibrated for 7 column volumes (CV) with buffer A. The application containing protGASE was loaded on the column and unbound sample was washed out with buffer A for 10 CV. A linear gradient from 0-100% buffer B for 30 column volumes was used to elute the protGASE. A peak containing protGASE was eluted with approximately 0.05 M NaCl concentration from the column. Collected fractions were analyzed by SDS PAGE and the identity of protGASE was confirmed using LC-MS analysis, which gave a mass very close to the expected theoretical mass of the protein Removal of the Prodomain Using the pACSH238 or pACSH239 Protease Fractions from the first purification step containing protGASE was pooled and the buffer was changed to a cleavage buffer with 50 mM Tris HCl pH 7.5, 150 mM NaCl and 1 mM DTT using Vivaspin 20 (10000 MWCO) (Satorius) for diafiltration. The amount of purified protGASE and pACSH239 protease was adjusted by estimating UV214 nm absorbance peak areas from HPLC chromatograms. Cleavage tests with different enzyme to substrate ratios (1:10, 1:50, 1:100 and 1:200) were performed with or without 1 mM DTT in the cleavage buffer at 25° C. overnight. Experiments showed that the pACSH239 protease was able to remove the prodomain completely (to obtain a Gly-Pro extended mature tGASE) using an enzyme substrate ration of 1:200 and 1 mM DTT in the cleavage buffer. The mass of the released mature tGASE and the protGASE was determined using LC-MS.

In similar tests, the pACSH238 protease was also found able to efficiently cleave off the prodomain from the protGASE.

Purification of the Mature tGASE:

The Gly-Pro extended mature tGASE obtained after digestion with the pACSH239 protease was diluted to 48 ml in 25 mM NaPO4 pH 6, 1 mM DTT (buffer A) and separated on a 5 ml SP Sepharose High Performance (HP) HiTrap column (GE Healthcare) using the following buffers:

Buffer A: 25 mM $NaPO_4$ buffer pH6.0+1 mM DTT

Buffer B: 25 mM $NaPO_4$ buffer pH6.0+1 mM DTT+0.5M NaCl

Purification was performed using a flow rate of 3 ml/min and linear gradient elution from 0-100% buffer B for 30 column volumes.

UV280 chromatograms from purification indicated that one single major peak was eluted from the SP Sepharose HP column at a NaCl conc. of approx. 0.1 M. LC-MS analysis confirmed the identity of the eluted protein to be mature tGASE. The pACSH239 protease was, due to the high charge of the N-terminally fused SEQ ID NO:19 tag, eluted from the column much later than the mature tGASE and could thus be efficiently removed from the target protein following a second purification step.

Example 4

Synthesis of a HAV18 3C Protease Encoding Sequence Using Overlap PCR:

The amino acid sequence of the mature Hepatitis A strain 18 (HAV18) 3C protease is as follows:

```
                                           (SEQ ID NO: 45)
STLEIAGLVRKNLVQFGVGEKNGCVRWVMNALGVKDDWLLVPSHAY

KFEKDYEMMEFYFNRGGTYYSISAGNVVIQSLDVGFQDVVLMKVPT

IPKFRDITEHFIKKGDVPRALNRLATLVTTVNGTPMLISEGPLKME

EKATYVHKKNDGTTVDLTVDQAWRGKGEGLPGMCGGALVSSNQSIQ

NAILGIHVAGGNSILVAKLVTQEMFQNIDKKIESQ.
```

A codon-optimized DNA fragment of mature HAV18 3C protease gene was obtained using splicing by overlap extension PCR methodology with two consecutive steps of PCR as described in example 1 for the HRV14 3C protease. The final fragment with correct sequence contained a 5'-end XhoI and 3' end BamHI site, which allowed ligation into pET11a vectors (Novagen) so that the SEQ ID NO:10 encoding part was linked to the 5-end of the linker and protease encoding region.

| Product name | Tag | Linker | Processing enzyme |
|---|---|---|---|
| pACSH362 | SEQ ID NO: 10 | SEQ ID NO: 47 | SEQ ID NO: 45 |

Expression of SEQ ID NO: 10 Tagged HAV18 3C Proteases (pACSH362)

Expression in Rosetta (DE3) *E. coli* strains was performed essentially as described in example 1. An expression level similar to SEQ ID NO:10 tagged HRV14 3C protease was achievable and at least 80% of the protein was in the soluble fraction after cell disruption and centrifugation.

Purification of SEQ ID NO: 10TaggedHAV18 3C Protease (pACSH362)

Cell culture pellets (from 80 ml of culture) of the pACSH362 protease were disrupted by ultrasonication in a buffer containing 25 mM NaPO$_4$ pH 7. Cell debris was spun down by centrifugation at 10.000 g. Supernatants were sterilefiltrated before purification, which was carried out using a AKTA explorer 100 purification system (GE Healthcare). A prepacked SP Sepharose FF HiTrap column with a 5 ml column volume (GE Healthcare) was used for the separation at a flowrate of 3 ml/min using the following buffers:

Buffer A: 50 mM sodium phosphate, pH 7
Buffer B: 50 mM sodium phosphate, pH 7+1M NaCl The column was initially equilibrated for 7 column volumes of buffer A. After loading of the application, unbound protein was removed by washing using 7 column volumes of buffer A. A linear gradient from 0-100% buffer B for 20 column volumes was used to elute the pACSH362 protease from the column. The pACSH362 protease was eluted from the column at a salt concentration of 0.2-0.3 M NaCl. The major part of the pACSH362 protease bond to the column at these purification conditions. Purity of the eluted pACSH362 protease was estimated to ~85-90% as determined by HPLC and SDS-PAGE standard methods after a single cation exchange chromatographic step. By LC-MS it was also verified that the eluted protease had a molecular weight as expected.

Evaluation of the Activity of SEQ ID NO:10 Tagged HAV18 3C Protease (pACSH362)

The tagged HAV18 3C protease (pACSH362) was used to process the pACSH360 fusion protein comprising the S661 insulin receptor antagonist peptide (SEQ ID NO: 37) with a N-terminal tag (SEQ ID NO: 19) and an intervening linker with a modified HAV 18 3C cleavage site SSSGGSELRTQ (SEQ ID NO: 49).

A 1:10 or 1:50 enzyme to substrate ratio of the pACSH362 protease and pACSH360 fusion protein was evaluated by LC-MS after incubation for 7 hours at 37° C. A fragment representing the released S661 peptide was observed for both ratios, as in example 1, showing that the tagged HAV18 enzyme is active.

Example 5

Cloning of Tagged Rabbit Hemorrhagic Disease Virus 3C-Like Protease

Purification protein tags from ribosomal protein L9 family coming from *Thermus thermophilus, Geobacillus kaustophilus, Thermosipho melanesiensis*, BI429 and *Acidothermus cellulolyticus* 11 B were codon optimised for expression *E. coli* and obtained as synthetic genes from GENEART GmbH, Regensburg, Germany. The gene fragments encoding the tags had an 5' end NdeI site and a 3' end XhoI site. A codon optimised fragment with a 5'-end XhoI site and a 3'-end BamHI site encoding the Rabbit Hemorrhagic Disease Virus 3C-like protease (RHDV) was also obtained (GENEART GmbH, Regensburg, Germany).

The following constructs were assembled by means of standard cloning techniques in the pET11a *E. coli* expression vector in order to generate the following RHDV protease variants:

| Product name | Tag | Linker | Processing enzyme |
|---|---|---|---|
| pACSH433 | SEQ ID NO: 41 | SEQ ID NO: 48 | SEQ ID NO: 46 |
| pACSH434 | SEQ ID NO: 42 | SEQ ID NO: 48 | SEQ ID NO: 46 |
| pACSH435 | SEQ ID: NO: 43 | SEQ ID NO: 48 | SEQ ID NO: 46 |
| pACSH436 | SEQ ID: NO: 44 | SEQ ID NO: 48 | SEQ ID NO: 46 |

Expression of Tagged Rabbit Hemorrhagic Disease Virus 3C-Like Protease

Expression in BL21 (DE3) *E. coli* strains was performed essentially as described in example 1. Very similar expression levels were obtained for all four constructs and the solubility range from about 80%-90% as judged by SDS-PAGE of supernatants and pellets derived after cell disruption and centrifugation.

Purification of SEQ ID NO: 41, 42, 43 and 44 Tagged HAV18 3C Proteases.

Cell culture pellets (from 80 ml of culture) of each of the tagged RHDV proteases were disrupted by ultrasonication. Supernatants were prepared and separated using a prepacked SP Sepharose FF 5 ml column (GE Healthcare) using the same buffers and conditions as described previously.

Upon comparison of recovered amounts of the protease after the capture step, the best result was achieved with the pACSH433 protease comprising the SEQ ID NO: 41 tag, which bound ~2-3.5 times more protein on the column than for the remaining variants.

Example 6

Coexpression of Tagged HRV14 3C Protease Variant Together with protGASE (pNNC130) or pACSH294 (S661 Fusion Protein)

The pACYCDuet-1 plasmid (Novagen) has a lower copy number than pET11a (Novagen) plasmid and the amount of protein produced from this plasmid should be lower than the pET11a plasmid. Furthermore, the plasmid contains a different selection marker (chloramphinicol resistance) than pET11a allowing maintenance and co-expression from these two plasmids in the same host strain. It was evaluated whether a method for processing of target protein precursors using tagged processing enzymes was feasible using the pACYCDuet-1 vector for the expression of pACSH238 protease and the pET11a vector for the expression of protGASE (pNNC130) or S661 fusion protein (pACSH294) that can be processed by the pACSH238 protease.

A fragment from the pET11a plasmid encoding pACSH238 protease (Example 1) and a part of the vector backbone upstream of the start codon was excised with MluI and BamHI restriction enzymes and ligated into the MluI/BamHI cleaved pACYCDuet-1 plasmid backbone (Novagen).

The pACYCDuet1 plasmid expressing the pACSH238 protease was transformed into BL21 (DE3) together with either the pET11a plasmid encoding the protGASE (pNNC130) or the S661 fusion protein (pACSH294) Thus, one strain can co-express the pACSH238 protease (from the pACYC-Duet-1 plasmid) together with the protGASE and the other strain expresses the pACSH238 protease together with S661 fusion protein (pACSH294).

The co-expressing strains were cultivated in LB medium containing 150 micrograms per milliliter ampicillin and 34 micrograms per milliliter chloramphinicol. in parallel with control strains expressing either the protGASE or the S661 fusion protein alone. Expression conditions were as described for the pACSH238 protease in example 1. After 3 hours expression at 30° C. the co-expressing strains and their controls were harvested. From SDS-PAGE it was apparent that co-expression resulted in a lower molecular weight for the induced protGASE or S661 fusion protein compared to the controls. The truncated induced protein present in the SDS gel band from the pACSH238 protease/protGASE co-expressing strain was identified as tGASE using standard mass spectrometry based methods following in-gel digestion. The results therefore show that the co expressed pACSH238 protease was able to cleave off the prodomain from the pro-tGASE and the SEQ ID NO:19 purification tag from the S661 fusion protein in vivo.

The invention claimed is:

1. A processing enzyme comprising an N-terminally attached tag derived from a ribosomal protein from a thermophilic bacteria, wherein at least 15% of the protein's amino acids comprise Lys, Arg or a combination thereof, wherein the tag is attached to the processing enzyme by a linker sequence consisting of SEQ ID NO: 47.

2. The processing enzyme according to claim 1, wherein the tag comprises no cysteine residues.

3. The processing enzyme according to claim 1, wherein the tag comprises from 50 to 250 amino acid residues.

4. The processing enzyme according to claim 1, wherein the tag comprises from 75 to 200 amino acid residues.

5. The processing enzyme according to claim 1, wherein the tag comprises from 100 to 250 amino acid residues.

6. The processing enzyme according to claim 1, wherein the tag comprises from 100 to 200 amino acid residues.

7. The processing enzyme according to claim 1, wherein 15% to 50% of the amino acid residues in the tag comprise Lys, Arg, or a combination thereof.

8. The processing enzyme according to claim 1, wherein 20% to 50% of the amino acid residues in the tag comprise Lys, Arg, or a combination thereof.

9. The processing enzyme according to claim 1, wherein 30% to 50% of the amino acid residues in the tag comprise Lys, Arg, or a combination thereof.

10. The processing enzyme according to claim 1, wherein 40% to 50% of the amino acid residues in the tag comprise Lys, Arg, or a combination thereof.

11. The processing enzyme according to claim 1, wherein 35% to 50% of the amino acid residues in the tag comprise Lys, Arg, or a combination thereof.

12. The processing enzyme according to claim 1, wherein the tag is derived from a large ribosomal subunit protein L9.

13. The processing enzyme according to claim 12, wherein the tag is selected from the group of peptide sequences consisting of SEQ ID NO:10, SEQ ID NO: 41, SEQ ID NO: 42, SEQ ID NO: 43 and SEQ ID NO: 44.

14. The processing enzyme according to claim 1, selected from oxidoreductases, transferases, hydrolases, lyases, isomerases and ligases.

15. A method for making a tagged processing enzyme according to claim 1, comprising i) expressing the processing enzyme comprising the N-terminal tag derived from a ribosomal protein from a thermophilic bacteria in a suitable expression host, wherein at least 15% of the protein's amino acids comprise Lys, Arg or a combination thereof, ii) loading the expressed processing enzyme comprising the N-terminal tag on a cation-exchange column, iii) and eluting the processing enzyme comprising the N-terminal tag with a suitable eluent.

16. The method according to claim 15, wherein the processing enzyme is a protease selected from the group consisting of Human Rhino Virus Strain 14 (HRV14) 3C protease, Hepatitis A strain 18 (HAV18) 3C, Tobacco Etch Virus (TEV) protease or Rabbit Hemorrhagic Disease Virus (RHDV) 3C protease.

17. The method according to claim 15, wherein the tag is selected from the group consisting of SEQ ID NO: 10, SEQ ID NO: 41, SEQ ID NO: 42, SEQ ID NO: 43 and SEQ ID NO: 44.

18. A method for modifying a target protein precursor comprising the steps of contacting the processing enzyme comprising the N-terminal tag according to claim 1 with the target protein precursor and separating the resulting target protein from the processing enzyme.

19. The method according to claim 18, wherein the processing enzyme comprising the N-terminal tag and the target protein precursor are co-expressed in a suitable host enabling isolation of the target protein after expression.

\* \* \* \* \*

SEQUENCE LISTING

<160> NUMBER OF SEQ ID NOS: 49

<210> SEQ ID NO 1
<211> LENGTH: 56
<212> TYPE: PRT
<213> ORGANISM: Bacillus stearothermophilus

<400> SEQUENCE: 1

Met Ser Lys Thr Ile Val Arg Lys Asn Glu Ser Ile Asp Asp Ala Leu
1               5                   10                  15

Arg Arg Phe Lys Arg Ala Val Ser Lys Thr Gly Thr Leu Gln Glu Val
            20                  25                  30

Arg Lys Arg Glu Phe Tyr Glu Lys Pro Ser Val Arg Arg Lys Lys Lys
        35                  40                  45

Ser Glu Ala Ala Arg Lys Arg Lys
    50                  55

<210> SEQ ID NO 2
<211> LENGTH: 50
<212> TYPE: PRT
<213> ORGANISM: Archaeoglobus fulgidus

<400> SEQUENCE: 2

Met Gly Lys Lys Thr Val Gly Val Lys Lys Arg Leu Ala Lys Ala Tyr
1               5                   10                  15

Lys Gln Asn Arg Arg Ala Pro Val Trp Ile Thr Val Lys Thr Lys Arg
            20                  25                  30

Ser Val Phe Gly Ser Pro Lys Arg Arg His Trp Arg Arg Ser Lys Leu
        35                  40                  45

Lys Val
    50

<210> SEQ ID NO 3
<211> LENGTH: 44
<212> TYPE: PRT
<213> ORGANISM: Thermotoga maritima

<400> SEQUENCE: 3

Met Lys Arg Thr Tyr Gln Pro Ser Arg Arg Lys Arg Lys Arg Thr His
1               5                   10                  15

Gly Phe Leu Ala Arg Lys Arg Thr Pro Gly Gly Arg Arg Val Leu Lys
            20                  25                  30

Asn Arg Arg Arg Lys Gly Arg Trp Arg Leu Thr Val
        35                  40

<210> SEQ ID NO 4

```
<211> LENGTH: 27
<212> TYPE: PRT
<213> ORGANISM: Thermus thermophilus

<400> SEQUENCE: 4

Met Gly Lys Gly Asp Arg Arg Thr Arg Arg Gly Lys Ile Trp Arg Gly
1               5                   10                  15

Thr Tyr Gly Lys Tyr Arg Pro Arg Lys Lys
            20                  25

<210> SEQ ID NO 5
<211> LENGTH: 67
<212> TYPE: PRT
<213> ORGANISM: Thermotoga maritima

<400> SEQUENCE: 5

Met Ala Lys Val Lys Met Lys Thr Asn Arg Ser Ala Ala Lys Arg Phe
1               5                   10                  15

Lys Val Thr Ala Lys Gly Lys Ile Lys Arg Trp Lys Ser Gly Gly Ala
            20                  25                  30

His Tyr Asn Thr Lys Lys Ser Ser Lys Arg Lys Arg His Leu Arg Lys
        35                  40                  45

His Thr Tyr Val Lys Asp Asn Met Leu Lys His Val Lys Ala Leu Leu
    50                  55                  60

Lys Glu Phe
65

<210> SEQ ID NO 6
<211> LENGTH: 233
<212> TYPE: PRT
<213> ORGANISM: Thermotoga maritima

<400> SEQUENCE: 6

Met Pro Lys His Ser Lys Arg Tyr Leu Glu Ala Arg Lys Leu Val Asp
1               5                   10                  15

Arg Thr Lys Tyr Tyr Asp Leu Asp Glu Ala Ile Glu Leu Val Lys Lys
            20                  25                  30

Thr Ala Thr Ala Lys Phe Asp Glu Thr Ile Glu Leu His Ile Gln Thr
        35                  40                  45

Gly Ile Asp Tyr Arg Lys Pro Glu Gln His Ile Arg Gly Thr Ile Val
    50                  55                  60

Leu Pro His Gly Thr Gly Lys Glu Val Lys Val Leu Val Phe Ala Lys
65                  70                  75                  80

Gly Glu Lys Ala Lys Glu Ala Leu Glu Ala Gly Ala Asp Tyr Val Gly
                85                  90                  95

Ala Glu Asp Leu Val Glu Lys Ile Glu Lys Gly Phe Leu Asp Phe
                100                 105                 110

Asp Val Ala Ile Ala Thr Pro Asp Met Met Arg Ile Ile Gly Arg Leu
            115                 120                 125

Gly Lys Ile Leu Gly Pro Arg Gly Leu Met Pro Ser Pro Lys Ser Gly
        130                 135                 140

Thr Val Thr Gln Glu Val Ala Glu Ala Val Lys Glu Phe Lys Lys Gly
145                 150                 155                 160

Arg Ile Glu Val Arg Thr Asp Lys Thr Gly Asn Ile His Ile Pro Val
                165                 170                 175

Gly Lys Arg Ser Phe Asp Asn Glu Lys Leu Lys Glu Asn Ile Ile Ala
            180                 185                 190

Ala Ile Lys Gln Ile Met Gln Met Lys Pro Ala Gly Val Lys Gly Gln
```

```
            195                 200                 205
Phe Ile Lys Lys Val Val Leu Ala Ser Thr Met Gly Pro Gly Ile Lys
210                 215                 220

Leu Asn Leu Gln Ser Leu Leu Lys Glu
225                 230

<210> SEQ ID NO 7
<211> LENGTH: 235
<212> TYPE: PRT
<213> ORGANISM: Thermotoga maritima

<400> SEQUENCE: 7

Met Ala Gln Val Asp Leu Leu Asn Val Lys Gly Glu Lys Val Gly Thr
1               5                   10                  15

Leu Glu Ile Ser Asp Phe Val Phe Asn Ile Asp Pro Asn Tyr Asp Val
                20                  25                  30

Met Trp Arg Tyr Val Asp Met Gln Leu Ser Asn Arg Arg Ala Gly Thr
            35                  40                  45

Ala Ser Thr Lys Thr Arg Gly Glu Val Ser Gly Gly Arg Lys Pro
        50                  55                  60

Trp Pro Gln Lys His Thr Gly Arg Ala Arg His Gly Ser Ile Arg Ser
65                  70                  75                  80

Pro Ile Trp Arg His Gly Gly Val Val His Gly Pro Lys Pro Arg Asp
                85                  90                  95

Trp Ser Lys Lys Leu Asn Lys Lys Met Lys Lys Leu Ala Leu Arg Ser
            100                 105                 110

Ala Leu Ser Val Lys Tyr Arg Glu Asn Lys Leu Leu Val Leu Asp Asp
        115                 120                 125

Leu Lys Leu Glu Arg Pro Lys Thr Lys Ser Leu Lys Glu Ile Leu Gln
    130                 135                 140

Asn Leu Gln Leu Ser Asp Lys Lys Thr Leu Ile Val Leu Pro Trp Lys
145                 150                 155                 160

Glu Glu Gly Tyr Met Asn Val Lys Leu Ser Gly Arg Asn Leu Pro Asp
                165                 170                 175

Val Lys Val Ile Ile Ala Asp Asn Pro Asn Asn Ser Lys Asn Gly Glu
            180                 185                 190

Lys Ala Val Arg Ile Asp Gly Leu Asn Val Phe Asp Met Leu Lys Tyr
        195                 200                 205

Asp Tyr Leu Val Leu Thr Arg Asp Met Val Ser Lys Ile Glu Glu Val
    210                 215                 220

Leu Gly Asn Glu Ala Gly Lys Ala Leu Thr Ala
225                 230                 235

<210> SEQ ID NO 8
<211> LENGTH: 184
<212> TYPE: PRT
<213> ORGANISM: Thermotoga maritima

<400> SEQUENCE: 8

Met Arg Tyr Glu Tyr Val Pro Leu Lys Asp Gln Tyr Glu Lys Glu Ile
1               5                   10                  15

Val Pro Ala Leu Met Lys Glu Phe Asn Tyr Lys Asn Ile His Gln Val
                20                  25                  30

Pro Lys Leu Val Lys Ile Val Asn Met Gly Ile Gly Glu Gly Ser
            35                  40                  45

Arg Asn Tyr Asp Leu Ile Glu Arg His Ala Asn Glu Leu Ala Lys Ile
    50                  55                  60
```

Thr Gly Gln Lys Pro Ile Val Thr Arg Ala Arg Lys Ser Ile Ser Asn
65                  70                  75                  80

Phe Lys Ile Arg Lys Gly Met Pro Ile Gly Leu Lys Val Thr Leu Arg
                85                  90                  95

Gly Ala Arg Met Tyr Asn Phe Leu Tyr Lys Leu Ile Asn Ile Val Leu
            100                 105                 110

Pro Lys Val Arg Asp Phe Arg Gly Leu Asp Pro Asn Ser Phe Asp Gly
        115                 120                 125

Arg Gly Asn Tyr Ser Phe Gly Leu Ser Glu Gln Leu Val Phe Pro Glu
    130                 135                 140

Leu Asn Pro Asp Glu Val Arg Arg Ile Gln Gly Met Asp Ile Thr Ile
145                 150                 155                 160

Val Thr Thr Ala Lys Thr Asp Gln Glu Ala Arg Arg Leu Leu Glu Leu
                165                 170                 175

Phe Gly Met Pro Phe Lys Arg Gly
            180

<210> SEQ ID NO 9
<211> LENGTH: 184
<212> TYPE: PRT
<213> ORGANISM: Thermotoga maritima

<400> SEQUENCE: 9

Met Ser Arg Leu Ala Lys Lys Pro Ile Val Leu Pro Gln Gly Val Thr
1               5                   10                  15

Val Glu Ile Lys Asp Asn Val Val Lys Val Lys Gly Pro Lys Gly Glu
                20                  25                  30

Leu Ser Gln Glu Phe Leu Pro Tyr Val Lys Ile Glu Val Glu Gly Asn
            35                  40                  45

Glu Val Trp Val Arg Pro Asn Glu Glu Gln Ile Ile Arg Lys Ser Asp
        50                  55                  60

Trp Arg Lys Val Lys Met Phe Gln Gly Thr Tyr Trp Ser Leu Ile Arg
65                  70                  75                  80

Asn Met Val Val Gly Val Thr Glu Gly Tyr Lys Lys Glu Leu Glu Ile
                85                  90                  95

Val Gly Ile Gly Tyr Arg Ala Gln Leu Gln Gly Asn Thr Leu Val Met
            100                 105                 110

Asn Leu Gly Tyr Ala His Pro Val Val Tyr Glu Ile Pro Ser Asp Val
        115                 120                 125

Lys Ile Glu Val Pro Ala Pro Asn Arg Ile Ile Val Ser Gly Ile Asp
    130                 135                 140

Lys Gln Arg Val Gly Gln Val Ala Ala Glu Ile Arg Ala Phe Arg Pro
145                 150                 155                 160

Pro Asn Val Tyr Thr Gly Lys Gly Ile Arg Tyr Val Gly Glu Val Val
                165                 170                 175

Arg Gln Lys Glu Gly Lys Lys Ala
            180

<210> SEQ ID NO 10
<211> LENGTH: 149
<212> TYPE: PRT
<213> ORGANISM: Thermotoga maritima

<400> SEQUENCE: 10

Met Lys Val Ile Leu Leu Arg Asp Val Pro Lys Ile Gly Lys Lys Gly
1               5                   10                  15

```
Glu Ile Lys Glu Val Ser Asp Gly Tyr Ala Arg Asn Tyr Leu Ile Pro
            20                  25                  30

Arg Gly Phe Ala Lys Glu Tyr Thr Glu Gly Leu Glu Arg Ala Ile Lys
        35                  40                  45

His Glu Lys Glu Ile Glu Lys Arg Lys Lys Glu Arg Glu Arg Glu Glu
    50                  55                  60

Ser Glu Lys Ile Leu Lys Glu Leu Lys Lys Arg Thr His Val Val Lys
65                  70                  75                  80

Val Lys Ala Gly Glu Gly Gly Lys Ile Phe Gly Ala Val Thr Ala Ala
                85                  90                  95

Thr Val Ala Glu Glu Ile Ser Lys Thr Thr Gly Leu Lys Leu Asp Lys
            100                 105                 110

Arg Trp Phe Lys Leu Asp Lys Pro Ile Lys Glu Leu Gly Glu Tyr Ser
        115                 120                 125

Leu Glu Val Ser Leu Pro Gly Gly Val Lys Asp Thr Ile Lys Ile Arg
    130                 135                 140

Val Glu Arg Glu Glu
145
```

<210> SEQ ID NO 11
<211> LENGTH: 179
<212> TYPE: PRT
<213> ORGANISM: Thermotoga maritima

<400> SEQUENCE: 11

```
Met Leu Thr Arg Gln Gln Lys Glu Leu Ile Val Lys Glu Met Ser Glu
1               5                   10                  15

Ile Phe Lys Lys Thr Ser Leu Ile Leu Phe Ala Asp Phe Leu Gly Phe
            20                  25                  30

Thr Val Ala Asp Leu Thr Glu Leu Arg Ser Arg Leu Arg Glu Lys Tyr
        35                  40                  45

Gly Asp Gly Ala Arg Phe Arg Val Val Lys Asn Thr Leu Leu Asn Leu
    50                  55                  60

Ala Leu Lys Asn Ala Glu Tyr Glu Gly Tyr Glu Glu Phe Leu Lys Gly
65                  70                  75                  80

Pro Thr Ala Val Leu Tyr Val Thr Glu Gly Asp Pro Val Glu Ala Val
                85                  90                  95

Lys Ile Ile Tyr Asn Phe Tyr Lys Asp Lys Lys Ala Asp Leu Ser Arg
            100                 105                 110

Leu Lys Gly Gly Phe Leu Glu Gly Lys Lys Phe Thr Ala Glu Glu Val
        115                 120                 125

Glu Asn Ile Ala Lys Leu Pro Ser Lys Glu Glu Leu Tyr Ala Met Leu
    130                 135                 140

Val Gly Arg Val Lys Ala Pro Ile Thr Gly Leu Val Phe Ala Leu Ser
145                 150                 155                 160

Gly Ile Leu Arg Asn Leu Val Tyr Val Leu Asn Ala Ile Lys Glu Lys
                165                 170                 175

Lys Ser Glu
```

<210> SEQ ID NO 12
<211> LENGTH: 149
<212> TYPE: PRT
<213> ORGANISM: Thermotoga maritima

<400> SEQUENCE: 12

```
Met Ala Arg Tyr Phe Pro Val Gln Lys Thr Thr Met Ile Lys Pro Glu
1               5                   10                  15
```

Glu Val Glu Arg Lys Trp Tyr Val Asp Ala Ser Gly Lys Val Leu
            20                  25                  30

Gly Arg Leu Ala Thr Arg Ile Ala Lys Ile Leu Met Gly Lys His Lys
        35                  40                  45

Pro Asn Tyr Thr Pro His Val Asp Thr Gly Asp Tyr Val Ile Val Val
    50                  55                  60

Asn Ala Asp Lys Val Val Leu Thr Gly Lys Lys Leu Asp Gln Lys Val
65                  70                  75                  80

Tyr Tyr Trp His Ser Gly Tyr Pro Gly Gly Leu Lys Ser Leu Thr Ala
                85                  90                  95

Arg Gln Met Leu Glu Lys His Pro Glu Arg Leu Ile Trp Leu Ala Val
            100                 105                 110

Lys Arg Met Leu Pro Lys Asn Arg Lys Gly Arg Lys Met Leu Lys Arg
        115                 120                 125

Leu Lys Val Tyr Ala Ser Pro Glu His Pro His Gln Ala Gln Lys Pro
    130                 135                 140

Glu Pro Ile Glu Leu
145

<210> SEQ ID NO 13
<211> LENGTH: 147
<212> TYPE: PRT
<213> ORGANISM: Thermotoga maritima

<400> SEQUENCE: 13

Met Arg Leu Glu Asp Leu Arg Pro Thr Pro Gly Ala Met Lys Lys Arg
1               5                   10                  15

Lys Arg Val Gly Arg Gly Pro Gly Ser Gly His Gly Lys Thr Ser Gly
            20                  25                  30

Arg Gly His Lys Gly Gln Lys Ala Arg Gly Ser Gly Lys Val His Ile
        35                  40                  45

Trp Phe Glu Gly Gly Gln Thr Pro Leu Gln Arg Arg Leu Pro Lys Arg
    50                  55                  60

Gly Phe Lys Asn Ile Asn Lys Lys Val Tyr Ala Val Val Asn Val Lys
65                  70                  75                  80

Val Leu Glu Glu Arg Phe Glu Ala Asn Glu Glu Val Thr Pro Glu Lys
                85                  90                  95

Leu Ile Glu Arg Lys Ile Ile Lys Asp Leu Lys Asp Gly Val Lys Ile
            100                 105                 110

Leu Gly Asp Gly Glu Leu Thr Lys Pro Leu Val Val Lys Ala His Ala
        115                 120                 125

Phe Ser Lys Ser Ala Val Glu Lys Ile Glu Ser Ala Gly Gly Lys Ala
    130                 135                 140

Glu Val Ile
145

<210> SEQ ID NO 14
<211> LENGTH: 131
<212> TYPE: PRT
<213> ORGANISM: Thermotoga maritima

<400> SEQUENCE: 14

Met Arg His Arg Val Lys Arg His Lys Leu Gly Arg Tyr Gly Ser His
1               5                   10                  15

Arg Lys Ser Leu Leu Arg Asn Leu Ser Arg Glu Ile Val Glu His Gly
            20                  25                  30

```
Ser Ile Val Thr Thr Thr Ala Lys Ala Lys Ala Leu Lys Thr Phe Met
        35                  40                  45

Asp Lys Leu Val Ser Lys Ala Ile Glu Ala Ala Thr Thr Asp Asp Arg
    50                  55                  60

Ala Arg Ser Val His Leu Arg Arg Gln Ile Asn Ala Val Leu Gly Asp
65                  70                  75                  80

Arg Arg Leu Thr Asn Lys Leu Val Asp Glu Ile Ala Lys Asn Tyr Val
                85                  90                  95

Gly Arg Arg Gly Gly Tyr Val Arg Val Leu Arg Ile Gly Phe Arg Arg
                100                 105                 110

Gly Asp Ala Ala Glu Met Ser Leu Val Gln Leu Val Glu Ala Ser Ser
                115                 120                 125

Gln Glu Gly
    130

<210> SEQ ID NO 15
<211> LENGTH: 115
<212> TYPE: PRT
<213> ORGANISM: Thermotoga maritima

<400> SEQUENCE: 15

Met Asp His Leu Val Lys Ile Ile Glu Lys Lys Tyr Glu Lys Lys Glu
1               5                   10                  15

Ile Pro Asp Phe Arg Pro Gly Asp Thr Val Arg Val His Val Lys Val
                20                  25                  30

Ile Glu Gly Asp Arg Glu Arg Thr Gln Val Phe Glu Gly Ile Val Ile
            35                  40                  45

Ala Lys Arg Gly Ser Gly Ile Asn Lys Thr Phe Thr Val Arg Arg Ile
    50                  55                  60

Gly Ser His Gly Val Gly Val Glu Arg Ile Phe Pro Val His Ser Pro
65                  70                  75                  80

Val Val Glu Lys Ile Glu Val Val Arg Lys Gly Lys Val Arg Arg Ala
                85                  90                  95

Lys Leu Tyr Tyr Leu Arg Asn Val Arg Gly Lys Ile Arg Ile Lys Glu
                100                 105                 110

Arg Arg Asp
    115

<210> SEQ ID NO 16
<211> LENGTH: 118
<212> TYPE: PRT
<213> ORGANISM: Thermotoga maritima

<400> SEQUENCE: 16

Met Arg Val Lys Arg Ala Val His Ala Lys Lys Arg Lys Lys Tyr
1               5                   10                  15

Leu Lys Ala Ala Lys Gly Tyr Arg Gly Ala Leu Ser Arg Arg Tyr Lys
                20                  25                  30

Leu Ala Lys Gln Met Tyr Val Arg Ser Lys Trp Tyr Ser Tyr Val Gly
            35                  40                  45

Arg Lys Gln Lys Lys Arg Asp Met Arg Lys Leu Trp Ile Thr Arg Ile
    50                  55                  60

Asn Ile Ala Ala Arg Asn Glu Gly Leu Lys Tyr Ser Glu Leu Ile His
65                  70                  75                  80

Gly Leu Lys Leu Ala Gly Val Ser Ile Asn Arg Lys Met Leu Ser Glu
                85                  90                  95

Leu Ala Val Asn Asp Pro Glu Ala Phe Lys Glu Tyr Val Lys Ile Ala
```

Lys Glu Ala Leu Ala Ser
        115

<210> SEQ ID NO 17
<211> LENGTH: 105
<212> TYPE: PRT
<213> ORGANISM: Thermotoga maritima

<400> SEQUENCE: 17

Met Leu Tyr Ala Ile Val Glu Thr Ala Gly Arg Gln Tyr Arg Val Glu
1               5                   10                  15

Glu Gly Lys Ile Leu Tyr Thr Glu Lys Gln Lys Asp Tyr Ser Pro Gly
            20                  25                  30

Asp Glu Ile Val Phe Asp Arg Val Val Phe Val Arg Lys Asp Gly Glu
        35                  40                  45

Val Leu Val Gly Lys Pro Tyr Val Glu Gly Ala Lys Val Val Gly Lys
    50                  55                  60

Val Leu Glu His Ala Lys Ala Arg Lys Val Lys Thr Val Lys Tyr Arg
65                  70                  75                  80

Pro Arg Lys Asn Ser Lys Val Glu Lys Gly His Arg Gln Trp Tyr Thr
                85                  90                  95

Ala Ile Lys Ile Glu Lys Ile Glu Leu
            100                 105

<210> SEQ ID NO 18
<211> LENGTH: 100
<212> TYPE: PRT
<213> ORGANISM: Thermotoga maritima

<400> SEQUENCE: 18

Met Lys Gln Glu Lys Leu Ser Leu His Asp Val Leu Ile Arg Pro Ile
1               5                   10                  15

Ile Thr Glu Lys Ala Leu Ile Leu Arg Glu Gln Arg Lys Tyr Val Phe
            20                  25                  30

Glu Val Asn Pro Leu Ala Asn Lys Asn Leu Val Lys Glu Ala Val Glu
        35                  40                  45

Lys Leu Phe Asn Val Lys Val Glu Lys Val Asn Ile Leu Asn Met Lys
    50                  55                  60

Pro Lys Pro Lys Arg Arg Gly Ile Phe Glu Gly Lys Thr Arg Ser Trp
65                  70                  75                  80

Lys Lys Ala Val Val Thr Leu Lys Glu Gly Tyr Thr Ile Lys Glu Leu
                85                  90                  95

Glu Gly Glu His
            100

<210> SEQ ID NO 19
<211> LENGTH: 83
<212> TYPE: PRT
<213> ORGANISM: Thermotoga maritima

<400> SEQUENCE: 19

Met Ala His Lys Lys Ser Gly Gly Val Ala Leu Asn Gly Arg Asp Ser
1               5                   10                  15

Leu Pro Lys Tyr Leu Gly Val Lys Val Gly Asp Gly Gln Ile Val Lys
            20                  25                  30

Ala Gly Asn Ile Leu Val Arg Gln Arg Gly Thr Arg Phe Tyr Pro Gly
        35                  40                  45

```
Lys Asn Val Gly Met Gly Arg Asp Phe Thr Leu Phe Ala Leu Lys Asp
            50                  55                  60

Gly Arg Val Lys Phe Glu Thr Lys Asn Asn Lys Lys Tyr Val Ser Val
 65                  70                  75                  80

Tyr Glu Glu

<210> SEQ ID NO 20
<211> LENGTH: 66
<212> TYPE: PRT
<213> ORGANISM: Thermotoga maritima

<400> SEQUENCE: 20

Met Lys Ala Ser Glu Leu Arg Asn Tyr Thr Asp Glu Glu Leu Lys Asn
 1               5                  10                  15

Leu Leu Glu Glu Lys Lys Arg Gln Leu Met Glu Leu Arg Phe Gln Leu
            20                  25                  30

Ala Met Gly Gln Leu Lys Asn Thr Ser Leu Ile Lys Leu Thr Lys Arg
        35                  40                  45

Asp Ile Ala Arg Ile Lys Thr Ile Leu Arg Glu Arg Glu Leu Gly Ile
    50                  55                  60

Arg Arg
 65

<210> SEQ ID NO 21
<211> LENGTH: 67
<212> TYPE: PRT
<213> ORGANISM: Thermotoga maritima

<400> SEQUENCE: 21

Met Pro Lys Lys Leu Lys Ile Lys Leu Val Lys Ser Pro Ile Gly Tyr
 1               5                  10                  15

Ser Trp Asp Gln Lys Asp Thr Val Lys Arg Leu Gly Leu Lys Lys Leu
            20                  25                  30

Asn Gln Val Val Ile Lys Asp Asp Leu Pro Gln Ile Arg Gly Met Ile
        35                  40                  45

Arg Lys Val Lys His Leu Val Glu Val Glu Ile Glu Glu Gly Gly
    50                  55                  60

Ser Asn Ala
 65

<210> SEQ ID NO 22
<211> LENGTH: 65
<212> TYPE: PRT
<213> ORGANISM: Thermotoga maritima

<400> SEQUENCE: 22

Met Pro Lys Val Lys Thr Asn Arg Ser Ala Ala Lys Arg Phe Arg Ile
 1               5                  10                  15

Thr Lys Asn Gly Lys Ile Met Arg Asn His Ala Tyr Arg Ser His Lys
            20                  25                  30

Thr Gly Lys Lys Arg Arg Asn Ala Leu Arg Ala Leu Arg Lys Lys Asp
        35                  40                  45

Val Val Ser Ser Ala Asp Lys Asn Arg Val Leu Arg Leu Leu Gly Lys
    50                  55                  60

Lys
 65

<210> SEQ ID NO 23
<211> LENGTH: 209
```

```
<212> TYPE: PRT
<213> ORGANISM: Thermotoga maritima

<400> SEQUENCE: 23

Met Gly Gln Lys Val His Pro Arg Gly Phe Arg Leu Gly Leu Ser Ala
1               5                   10                  15

Asp Trp Gln Ala Lys Trp Phe Asn Glu Lys Asn Tyr Lys Glu Trp Leu
            20                  25                  30

Leu Glu Asp Glu Glu Ile Arg Lys Ile Ile Lys Asn Lys Tyr Tyr His
        35                  40                  45

Ala Gly Ile Ser Glu Ile Tyr Val Glu Arg Pro Asp Ala Glu Arg Ile
    50                  55                  60

Asn Ile Thr Val Lys Thr Ala Arg Pro Gly Ile Ile Gly Arg Lys
65                  70                  75                  80

Gly Ser Glu Ile Thr Ser Leu Arg Glu Leu Glu Arg Lys Phe Asn
                85                  90                  95

Arg Arg Val Val Ile Asn Ile Glu Glu Ile Lys Thr Pro Glu Leu Asp
            100                 105                 110

Ala Gln Leu Val Ala Glu Ser Ile Ala Ser Arg Ile Glu Lys Arg Ala
        115                 120                 125

Ser Tyr Lys Val Ala Met Lys Arg Ala Ile Met Asn Ala Met Arg Lys
    130                 135                 140

Gly Ala Gln Gly Ile Lys Val Met Val Ala Gly Arg Leu Gly Gly Ala
145                 150                 155                 160

Glu Ile Ala Arg Arg Glu Trp Tyr Leu Arg Gly Arg Leu Pro Leu Gln
                165                 170                 175

Lys Ile Lys Ala Ile Ile Asp Tyr Gly Thr Ala Thr Ala Trp Thr Lys
            180                 185                 190

Tyr Gly Thr Ile Gly Ile Lys Val Trp Ile Tyr Lys Gly Asp Ala Asp
        195                 200                 205

Ile

<210> SEQ ID NO 24
<211> LENGTH: 178
<212> TYPE: PRT
<213> ORGANISM: Thermotoga maritima

<400> SEQUENCE: 24

Met Glu Thr Gln Gly Val Met Lys Glu Ile Gln Tyr Glu Glu Phe Glu
1               5                   10                  15

Glu Lys Ile Ile Glu Ile Arg Arg Thr Ser Lys Val Thr Lys Gly Gly
            20                  25                  30

Lys Asn Leu Ser Phe Arg Val Val Ala Ile Val Gly Asn Lys Asn Gly
        35                  40                  45

Lys Val Gly Leu Gly Ile Gly Lys Ala Arg Glu Val Pro Glu Ala Ile
    50                  55                  60

Arg Lys Ala Ile Ser Ala Ala Lys Arg Asn Ile Val Glu Val Pro Val
65                  70                  75                  80

Ile Asn Gly Thr Ile Pro His Glu Val Ile Gly Arg Gln Asp Ala Ser
                85                  90                  95

Lys Val Leu Leu Lys Pro Ala Ala Pro Gly Thr Gly Ile Ile Ala Gly
            100                 105                 110

Gly Thr Val Arg Ala Val Val Glu Leu Ala Gly Ile Gln Asn Ile Leu
        115                 120                 125

Thr Lys Ser Leu Gly Ser Thr Asn Pro Leu Asn Leu Ala Leu Ala Thr
    130                 135                 140
```

```
Met Asn Gly Leu Lys Asn Leu Leu Asp Pro Arg Lys Val Ala Lys Leu
145                 150                 155                 160

Arg Asp Ile Ser Val Glu Val Phe Lys Gly Val Arg Arg Glu Asn
                165                 170                 175

Asn Ala

<210> SEQ ID NO 25
<211> LENGTH: 90
<212> TYPE: PRT
<213> ORGANISM: Thermotoga maritima

<400> SEQUENCE: 25

Met Val Ser Leu Asp Pro Glu Lys Lys Asn Glu Ile Ile Lys Glu Phe
1               5                   10                  15

Gln Ile His Glu Asn Asp Thr Gly Ser Val Glu Val Gln Ile Ala Leu
                20                  25                  30

Leu Thr Ala Arg Ile Lys His Leu Thr Glu His Leu Arg Lys His Pro
            35                  40                  45

Lys Asp Phe His Ser Arg Arg Gly Leu Met Lys Met Ile Gly Arg Arg
        50                  55                  60

Arg Lys Met Leu Lys Tyr Leu Arg His Lys Lys Pro Glu Val Tyr Arg
65                  70                  75                  80

Glu Leu Ile Ala Lys Leu Gly Ile Arg Lys
                85                  90

<210> SEQ ID NO 26
<211> LENGTH: 95
<212> TYPE: PRT
<213> ORGANISM: Thermotoga maritima

<400> SEQUENCE: 26

Met Gly Arg Ser Arg Lys Lys Gly Pro Tyr Val Asp Arg Lys Leu Leu
1               5                   10                  15

Glu Lys Ile Arg Lys Leu Asn Glu Thr Gly Glu Lys Lys Val Ile Lys
                20                  25                  30

Thr Trp Ser Arg Ala Ser Met Ile Ile Pro Glu Met Val Gly His Thr
            35                  40                  45

Ile Ala Val Tyr Asn Gly Met Lys His Ile Pro Val Tyr Ile Thr Glu
        50                  55                  60

Asn Met Ile Gly His Arg Leu Gly Glu Phe Ala Pro Thr Arg Arg Phe
65                  70                  75                  80

Gly Gly His Ala Asp Lys Lys Ala Lys Lys Gly Glu Leu Lys Lys
                85                  90                  95

<210> SEQ ID NO 27
<211> LENGTH: 96
<212> TYPE: PRT
<213> ORGANISM: Thermotoga maritima

<400> SEQUENCE: 27

Met Pro Asn Ile Lys Ser Ala Lys Lys Arg Val Arg Val Ser Glu Lys
1               5                   10                  15

Arg Arg Leu Arg Asn Lys Ala Tyr Lys Thr Phe Phe Lys Asn Arg Ile
                20                  25                  30

Lys Glu Val Leu Lys Ala Ile Glu Asn Lys Glu Pro Lys Glu Val Val
            35                  40                  45

Leu Glu Leu Thr Arg Lys Ala Gln Ala Ala Ile Asp Lys Ala Val Ser
        50                  55                  60
```

```
Lys Gly Val Ile His Lys Asn Gln Gly Ala Arg Arg Lys Ala Arg Leu
 65                  70                  75                  80

Phe Glu Lys Val Asn Glu Tyr Leu Arg Thr Leu Glu Thr Thr Gln Glu
                 85                  90                  95

<210> SEQ ID NO 28
<211> LENGTH: 12
<212> TYPE: PRT
<213> ORGANISM: Artificial Sequence
<220> FEATURE:
<223> OTHER INFORMATION: Linker 1

<400> SEQUENCE: 28

Ser Ser Ser Gly Ser Ser Gly Ser Gly Ser Ser
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Linker 2

<400> SEQUENCE: 29

Gly Gly Ser Ser Gly Gly Ser Ser
1               5

<210> SEQ ID NO 30
<211> LENGTH: 8
<212> TYPE: PRT
<213> ORGANISM: Artificial Sequence
<220> FEATURE:
<223> OTHER INFORMATION: Linker 3

<400> SEQUENCE: 30

Ser Ser Ser Gly Ser Gly Ser Gly
1               5

<210> SEQ ID NO 31
<211> LENGTH: 7
<212> TYPE: PRT
<213> ORGANISM: Artificial Sequence
<220> FEATURE:
<223> OTHER INFORMATION: Linker 4

<400> SEQUENCE: 31

Ala Leu Ala Leu Ala Leu Ala
1               5

<210> SEQ ID NO 32
<211> LENGTH: 9
<212> TYPE: PRT
<213> ORGANISM: Artificial Sequence
<220> FEATURE:
<223> OTHER INFORMATION: Linker 5

<400> SEQUENCE: 32

Ala Leu Ala Leu Ala Leu Ala Pro Ala
1               5

<210> SEQ ID NO 33
<211> LENGTH: 10
<212> TYPE: PRT
<213> ORGANISM: Artificial Sequence
<220> FEATURE:
<223> OTHER INFORMATION: Linker 6
```

```
<400> SEQUENCE: 33

Ser Ser Ser Ala Leu Ala Leu Ala Leu Ala
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Linker 7

<400> SEQUENCE: 34

Ser Gly Ser Gly Ser Gly Ser Gly Ser
1               5

<210> SEQ ID NO 35
<211> LENGTH: 182
<212> TYPE: PRT
<213> ORGANISM: Human rhinovirus 14

<400> SEQUENCE: 35

Gly Pro Asn Thr Glu Phe Ala Leu Ser Leu Leu Arg Lys Asn Ile Met
1               5                   10                  15

Thr Ile Thr Thr Ser Lys Gly Glu Phe Thr Gly Leu Gly Ile His Asp
            20                  25                  30

Arg Val Cys Val Ile Pro Thr His Ala Gln Pro Gly Asp Asp Val Leu
        35                  40                  45

Val Asn Gly Gln Lys Ile Arg Val Lys Asp Lys Tyr Lys Leu Val Asp
    50                  55                  60

Pro Glu Asn Ile Asn Leu Glu Leu Thr Val Leu Thr Leu Asp Arg Asn
65                  70                  75                  80

Glu Lys Phe Arg Asp Ile Arg Gly Phe Ile Ser Glu Asp Leu Glu Gly
                85                  90                  95

Val Asp Ala Thr Leu Val Val His Ser Asn Asn Phe Thr Asn Thr Ile
            100                 105                 110

Leu Glu Val Gly Pro Val Thr Met Ala Gly Leu Ile Asn Leu Ser Ser
        115                 120                 125

Thr Pro Thr Asn Arg Met Ile Arg Tyr Asp Tyr Ala Thr Lys Thr Gly
    130                 135                 140

Gln Cys Gly Gly Val Leu Cys Ala Thr Gly Lys Ile Phe Gly Ile His
145                 150                 155                 160

Val Gly Gly Asn Gly Arg Gln Gly Phe Ser Ala Gln Leu Lys Lys Gln
                165                 170                 175

Tyr Phe Val Glu Lys Gln
            180

<210> SEQ ID NO 36
<211> LENGTH: 11
<212> TYPE: PRT
<213> ORGANISM: Human rhinovirus 14

<400> SEQUENCE: 36

Ser Ser Ser Gly Gly Ser Glu Val Leu Phe Gln
1               5                   10

<210> SEQ ID NO 37
<211> LENGTH: 43
<212> TYPE: PRT
<213> ORGANISM: Homo sapiens

<400> SEQUENCE: 37
```

```
Gly Ser Leu Asp Glu Ser Phe Tyr Asp Trp Phe Glu Arg Gln Leu Gly
1               5                   10                  15

Gly Gly Ser Gly Gly Ser Ser Leu Glu Glu Glu Trp Ala Gln Ile Gln
            20                  25                  30

Cys Glu Val Trp Gly Arg Gly Cys Pro Ser Tyr
            35                  40
```

<210> SEQ ID NO 38
<211> LENGTH: 236
<212> TYPE: PRT
<213> ORGANISM: Tobacco etch virus

<400> SEQUENCE: 38

```
Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
            35                  40                  45

Arg Arg Asn Asn Gly Thr Leu Leu Val Gln Ser Leu His Gly Val Phe
50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
            115                 120                 125

Ser Cys Thr Phe Pro Ser Ser Asp Gly Ile Phe Trp Lys His Trp Ile
130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
            195                 200                 205

Val Leu Trp Gly Gly His Lys Val Phe Met Val Lys Pro Glu Glu Pro
210                 215                 220

Phe Gln Pro Val Lys Glu Ala Thr Gln Leu Met Asn
225                 230                 235
```

<210> SEQ ID NO 39
<211> LENGTH: 12
<212> TYPE: PRT
<213> ORGANISM: Tobacco etch virus

<400> SEQUENCE: 39

```
Ser Ser Ser Gly Gly Ser Glu Asn Leu Tyr Phe Gln
1               5                   10
```

<210> SEQ ID NO 40
<211> LENGTH: 385
<212> TYPE: PRT
<213> ORGANISM: Streptomyces mobaraensis

<400> SEQUENCE: 40

```
Met Asp Asn Gly Ala Gly Glu Glu Thr Lys Ser Tyr Ala Glu Thr Tyr
1               5                   10                  15

Arg Leu Thr Ala Asp Asp Val Ala Asn Ile Asn Ala Leu Asn Glu Ser
            20                  25                  30

Ala Pro Ala Ala Ser Ser Ala Gly Pro Ser Phe Arg Ala Pro Leu Glu
        35                  40                  45

Val Leu Phe Gln Gly Pro Asp Ser Asp Arg Val Thr Pro Pro Ala
    50                  55                  60

Glu Pro Leu Asp Arg Met Pro Asp Pro Tyr Arg Pro Ser Tyr Gly Arg
65                  70                  75                  80

Ala Glu Thr Val Val Asn Asn Tyr Ile Arg Lys Trp Gln Gln Val Tyr
                85                  90                  95

Ser His Arg Asp Gly Arg Lys Gln Gln Met Thr Glu Glu Gln Arg Glu
            100                 105                 110

Trp Leu Ser Tyr Gly Cys Val Gly Val Thr Trp Val Asn Ser Gly Gln
        115                 120                 125

Tyr Pro Thr Asn Arg Leu Ala Phe Ala Ser Phe Asp Glu Asp Arg Phe
    130                 135                 140

Lys Asn Glu Leu Lys Asn Gly Arg Pro Arg Ser Gly Glu Thr Arg Ala
145                 150                 155                 160

Glu Phe Glu Gly Arg Val Ala Lys Glu Ser Phe Asp Glu Glu Lys Gly
                165                 170                 175

Phe Gln Arg Ala Arg Glu Val Ala Ser Val Met Asn Arg Ala Leu Glu
            180                 185                 190

Asn Ala His Asp Glu Ser Ala Tyr Leu Asp Asn Leu Lys Lys Glu Leu
        195                 200                 205

Ala Asn Gly Asn Asp Ala Leu Arg Asn Glu Asp Ala Arg Ser Pro Phe
    210                 215                 220

Tyr Ser Ala Leu Arg Asn Thr Pro Ser Phe Lys Glu Arg Asn Gly Gly
225                 230                 235                 240

Asn His Asp Pro Ser Arg Met Lys Ala Val Ile Tyr Ser Lys His Phe
                245                 250                 255

Trp Ser Gly Gln Asp Arg Ser Ser Ala Asp Lys Arg Lys Tyr Gly
            260                 265                 270

Asp Pro Asp Ala Phe Arg Pro Ala Pro Gly Thr Gly Leu Val Asp Met
        275                 280                 285

Ser Arg Asp Arg Asn Ile Pro Arg Ser Pro Thr Ser Pro Gly Glu Gly
    290                 295                 300

Phe Val Asn Phe Asp Tyr Gly Trp Phe Gly Ala Gln Thr Glu Ala Asp
305                 310                 315                 320

Ala Asp Lys Thr Val Trp Thr His Gly Asn His Tyr His Ala Pro Asn
                325                 330                 335

Gly Ser Leu Gly Ala Met His Val Tyr Glu Ser Lys Phe Arg Asn Trp
            340                 345                 350

Ser Glu Gly Tyr Ser Asp Phe Asp Arg Gly Ala Tyr Val Ile Thr Phe
        355                 360                 365

Ile Pro Lys Ser Trp Asn Thr Ala Pro Asp Lys Val Lys Gln Gly Trp
    370                 375                 380

Pro
385

<210> SEQ ID NO 41
<211> LENGTH: 148
```

```
<212> TYPE: PRT
<213> ORGANISM: Thermus thermophilus

<400> SEQUENCE: 41

Met Lys Val Ile Leu Leu Glu Pro Leu Glu Asn Leu Gly Asp Val Gly
1               5                   10                  15

Gln Val Val Asp Val Lys Pro Gly Tyr Ala Arg Asn Tyr Leu Leu Pro
            20                  25                  30

Arg Gly Leu Ala Val Leu Ala Thr Glu Ser Asn Leu Lys Ala Leu Glu
        35                  40                  45

Ala Arg Ile Arg Ala Gln Ala Lys Arg Leu Ala Glu Arg Lys Ala Glu
    50                  55                  60

Ala Glu Arg Leu Lys Glu Ile Leu Glu Asn Leu Thr Leu Thr Ile Pro
65                  70                  75                  80

Val Arg Ala Gly Glu Thr Lys Ile Tyr Gly Ser Val Thr Ala Lys Asp
                85                  90                  95

Ile Ala Glu Ala Leu Ser Arg Gln His Gly Ile Thr Ile Asp Pro Lys
            100                 105                 110

Arg Leu Ala Leu Glu Lys Pro Ile Lys Glu Leu Gly Glu Tyr Val Leu
        115                 120                 125

Thr Tyr Lys Pro His Pro Glu Val Pro Ile Gln Leu Lys Val Ser Val
    130                 135                 140

Val Ala Gln Glu
145

<210> SEQ ID NO 42
<211> LENGTH: 149
<212> TYPE: PRT
<213> ORGANISM: Geobacillus kaustophilus

<400> SEQUENCE: 42

Met Lys Val Ile Phe Leu Lys Asp Val Lys Gly Lys Gly Lys Lys Gly
1               5                   10                  15

Glu Ile Lys Asp Val Ala Asp Gly Tyr Ala Asn Asn Phe Leu Phe Lys
            20                  25                  30

Gln Gly Leu Ala Ile Glu Ala Thr Pro Ala Asn Ile Lys Ala Leu Glu
        35                  40                  45

Ala Gln Lys Gln Lys Glu Gln Arg Gln Ala Ala Glu Glu Leu Ala Asn
    50                  55                  60

Ala Lys Lys Leu Lys Glu Glu Leu Glu Lys Leu Thr Val Glu Ile Pro
65                  70                  75                  80

Ala Lys Ala Gly Glu Gly Gly Arg Leu Phe Gly Ser Ile Thr Ser Lys
                85                  90                  95

Gln Ile Ala Glu Ala Leu Gln Ala Gln His Gly Leu Lys Leu Asp Lys
            100                 105                 110

Arg Lys Ile Glu Leu Ala Asp Ala Ile Arg Ser Leu Gly Tyr Thr Asn
        115                 120                 125

Val Pro Val Lys Leu His Pro Glu Val Thr Ala Thr Leu Lys Val His
    130                 135                 140

Val Lys Glu Gln Lys
145

<210> SEQ ID NO 43
<211> LENGTH: 151
<212> TYPE: PRT
<213> ORGANISM: Thermosipho melanesiensis

<400> SEQUENCE: 43
```

Met Lys Val Val Leu Leu Lys Asp Val Ser Lys Ile Gly Lys Gly
1               5                   10                  15

Glu Ile Lys Asn Val Ser Asp Gly Tyr Ala Arg Asn Tyr Leu Ile Pro
            20                  25                  30

Lys Gly Leu Ala Leu Glu Ala Thr Pro Arg Val Leu Lys Arg Leu Glu
        35                  40                  45

Ala Glu Lys Arg Lys Lys Glu Glu Lys Ile Gln Ile Lys Thr Gln
50                  55                  60

Asn Glu Glu Leu Leu Lys Met Leu Lys Lys Phe Leu Tyr Lys Ile Pro
65              70                  75                  80

Val Lys Ala Gly Glu Ser Gly Lys Leu Phe Gly Ala Leu Thr Asn Ser
                85                  90                  95

Asp Ile Ala Lys Ala Val Glu Lys Ile Ala Asp Val Asn Ile Asp Lys
                100                 105                 110

Lys Phe Ile Val Leu Glu Lys Pro Ile Lys Glu Ile Gly Met Tyr Asp
            115                 120                 125

Val Leu Val Arg Leu Pro Glu Gly Val Ser Gly Lys Ile Lys Val Glu
        130                 135                 140

Val Ile Gln Glu Gly Lys Asn
145                 150

<210> SEQ ID NO 44
<211> LENGTH: 149
<212> TYPE: PRT
<213> ORGANISM: Acidothermus cellulolyticus

<400> SEQUENCE: 44

Met Lys Leu Ile Leu Thr Gln Glu Val Ala Gly Leu Gly Gly Pro Gly
1               5                   10                  15

Asp Val Val Glu Val Arg Asp Gly Tyr Gly Arg Asn Tyr Leu Leu Pro
            20                  25                  30

Lys Arg Leu Ala Met Pro Ala Ser Pro Gly Ala Val Lys Gln Val Ala
        35                  40                  45

Leu Ile Lys Arg Ala Arg Glu Val Arg Glu Ile Arg Asp Leu Asp Gln
50                  55                  60

Ala Arg Ala Leu Arg Asp Gln Leu Glu Ala Leu Pro Val Thr Leu Pro
65              70                  75                  80

Ala Arg Ala Gly Ser Gly Gly Arg Leu Phe Gly Ser Val Thr Pro Asp
                85                  90                  95

Asp Ile Ala Ala Ala Val His Ala Gly Gly Pro Lys Leu Asp Lys
                100                 105                 110

Arg Arg Ile Glu Ile Ser Gly Pro Ile Lys Thr Ile Gly Ser His Gln
            115                 120                 125

Val Thr Val Arg Leu His Pro Glu Val Ser Ala Thr Val Ser Val Glu
        130                 135                 140

Val Val Pro Ala Ser
145

<210> SEQ ID NO 45
<211> LENGTH: 219
<212> TYPE: PRT
<213> ORGANISM: Hepatitis A virus

<400> SEQUENCE: 45

Ser Thr Leu Glu Ile Ala Gly Leu Val Arg Lys Asn Leu Val Gln Phe
1               5                   10                  15

Gly Val Gly Glu Lys Asn Gly Cys Val Arg Trp Val Met Asn Ala Leu
            20                  25                  30

Gly Val Lys Asp Asp Trp Leu Leu Val Pro Ser His Ala Tyr Lys Phe
        35                  40                  45

Glu Lys Asp Tyr Glu Met Met Glu Phe Tyr Phe Asn Arg Gly Gly Thr
    50                  55                  60

Tyr Tyr Ser Ile Ser Ala Gly Asn Val Val Ile Gln Ser Leu Asp Val
65              70                  75                  80

Gly Phe Gln Asp Val Val Leu Met Lys Val Pro Thr Ile Pro Lys Phe
                85                  90                  95

Arg Asp Ile Thr Glu His Phe Ile Lys Lys Gly Asp Val Pro Arg Ala
                100                 105                 110

Leu Asn Arg Leu Ala Thr Leu Val Thr Thr Val Asn Gly Thr Pro Met
            115                 120                 125

Leu Ile Ser Glu Gly Pro Leu Lys Met Glu Glu Lys Ala Thr Tyr Val
130                 135                 140

His Lys Lys Asn Asp Gly Thr Thr Val Asp Leu Thr Val Asp Gln Ala
145                 150                 155                 160

Trp Arg Gly Lys Gly Glu Gly Leu Pro Gly Met Cys Gly Gly Ala Leu
                165                 170                 175

Val Ser Ser Asn Gln Ser Ile Gln Asn Ala Ile Leu Gly Ile His Val
            180                 185                 190

Ala Gly Gly Asn Ser Ile Leu Val Ala Lys Leu Val Thr Gln Glu Met
        195                 200                 205

Phe Gln Asn Ile Asp Lys Lys Ile Glu Ser Gln
    210                 215

<210> SEQ ID NO 46
<211> LENGTH: 143
<212> TYPE: PRT
<213> ORGANISM: Rabbit hemorrhagic disease virus

<400> SEQUENCE: 46

Gly Leu Pro Gly Phe Met Arg His Asn Gly Ser Gly Trp Met Ile His
1               5                   10                  15

Ile Gly Asn Gly Leu Tyr Ile Ser Asn Thr His Thr Ala Arg Ser Ser
            20                  25                  30

Cys Ser Glu Ile Val Thr Cys Ser Pro Thr Thr Asp Leu Cys Leu Val
        35                  40                  45

Lys Gly Glu Ala Ile Arg Ser Val Ala Gln Ile Ala Glu Gly Thr Pro
    50                  55                  60

Val Cys Asp Trp Lys Lys Ser Pro Ile Ser Thr Tyr Gly Ile Lys Lys
65              70                  75                  80

Thr Leu Ser Asp Ser Thr Lys Ile Asp Val Leu Ala Tyr Asp Gly Cys
                85                  90                  95

Thr Gln Thr Thr His Gly Asp Cys Gly Leu Pro Leu Tyr Asp Ser Ser
                100                 105                 110

Gly Lys Ile Val Ala Ile His Thr Gly Lys Leu Leu Gly Phe Ser Lys
            115                 120                 125

Met Cys Thr Leu Ile Asp Leu Thr Ile Thr Lys Gly Val Tyr Glu
130                 135                 140

<210> SEQ ID NO 47
<211> LENGTH: 10
<212> TYPE: PRT
<213> ORGANISM: Artificial Sequence
<220> FEATURE:

```
<223> OTHER INFORMATION: Linker 8

<400> SEQUENCE: 47

Ser Ser Ser Gly Ser Gly Ser Gly Ser Gly
1               5               10

<210> SEQ ID NO 48
<211> LENGTH: 7
<212> TYPE: PRT
<213> ORGANISM: Artificial Sequence
<220> FEATURE:
<223> OTHER INFORMATION: Linker 9

<400> SEQUENCE: 48

Gly Ser Ser Gly Ser Gly Ser
1               5

<210> SEQ ID NO 49
<211> LENGTH: 11
<212> TYPE: PRT
<213> ORGANISM: Artificial Sequence
<220> FEATURE:
<223> OTHER INFORMATION: Linker 10

<400> SEQUENCE: 49

Ser Ser Ser Gly Gly Ser Glu Leu Arg Thr Gln
1               5               10
```